US008292786B1

United States Patent
Al-Tawil

(10) Patent No.: US 8,292,786 B1
(45) Date of Patent: Oct. 23, 2012

(54) WIRELESS HEAD SET FOR LINGUAL MANIPULATION OF AN OBJECT, AND METHOD FOR MOVING A CURSOR ON A DISPLAY

(76) Inventor: Youhanna Al-Tawil, Knoxville, TN (US)

( * ) Notice: Subject to any disclaimer, the term of this patent is extended or adjusted under 35 U.S.C. 154(b) by 0 days.

(21) Appl. No.: 13/315,885

(22) Filed: Dec. 9, 2011

(51) Int. Cl.
*A63B 71/00* (2006.01)
(52) U.S. Cl. ............... 482/1; 482/11; 600/587; 600/590
(58) Field of Classification Search ............... 482/1–11, 482/900–902; 701/1; 600/587–590; 434/185, 434/247
See application file for complete search history.

(56) References Cited

U.S. PATENT DOCUMENTS

| | | |
|---|---|---|
| 4,408,192 A | 10/1983 | Ward et al. |
| 4,562,432 A | 12/1985 | Sremac |
| 4,567,479 A | 1/1986 | Boyd |
| 4,629,424 A | 12/1986 | Lauks et al. |
| 4,697,601 A | 10/1987 | Durkee et al. |
| 4,746,913 A | 5/1988 | Volta |
| 4,758,829 A | 7/1988 | Smith, III |
| 4,783,656 A | 11/1988 | Katz et al. |
| 4,865,610 A | 9/1989 | Muller |
| 4,997,182 A | 3/1991 | Kussick |
| 5,212,476 A | 5/1993 | Maloney |
| 5,213,553 A | 5/1993 | Light |
| 5,422,640 A | 6/1995 | Haley |
| 5,452,727 A | 9/1995 | Tura et al. |
| 5,460,186 A | 10/1995 | Buchhold |
| 5,523,745 A | 6/1996 | Fortune et al. |
| 5,609,161 A | 3/1997 | Tura et al. |
| 5,689,246 A | 11/1997 | Dordick et al. |
| 5,830,235 A | 11/1998 | Standley |
| 5,904,140 A | 5/1999 | McGoogan |
| 5,954,673 A | 9/1999 | Staehlin et al. |
| 6,033,367 A | 3/2000 | Goldfield |
| 6,050,961 A | 4/2000 | Arnold |
| 6,108,592 A | 8/2000 | Kurtzberg et al. |
| 6,190,335 B1 | 2/2001 | Howard et al. |
| 6,222,524 B1 | 4/2001 | Salem et al. |
| 6,430,450 B1 | 8/2002 | Bach-y-Rita et al. |
| 6,511,441 B1 | 1/2003 | Wakumoto et al. |
| 6,702,765 B2 | 3/2004 | Robbins et al. |

(Continued)

OTHER PUBLICATIONS

Y. Takahashi, et al., High-speed Pressure Sensor Grid for Humanoid Robot Foot, IEEE/IROS (2005.

(Continued)

*Primary Examiner* — Glenn Richman
(74) *Attorney, Agent, or Firm* — Peter L. Brewer; Baker Donelson Bearman Caldwell & Berkowitz PC

(57) ABSTRACT

A head set is provided. The head set is beneficial for assisting an individual who is significantly impaired in the use of his or her upper extremities. The system enables this individual to move a cursor on a display of a computer or other processing device using lingual musculature. The head set includes a head piece. The head piece supports an articulating arm. The articulating arm supports a mouthpiece at a distal end. The mouthpiece has a plurality of cells embedded therein. The cells are configured to receive pressure applied by the tongue of the user. Movement of the tongue over and against the cells causes the cursor to be moved on the display. A method for moving a cursor on a display using a mouthpiece controlled through lingual movement is also provided. In addition, a method of typing characters on a virtual keyboard using lingual musculature is offered.

54 Claims, 9 Drawing Sheets

U.S. PATENT DOCUMENTS

| | | |
|---|---|---|
| 6,771,190 B2 | 8/2004 | Gordon |
| 6,801,231 B1 | 10/2004 | Beltz |
| 6,833,786 B1 | 12/2004 | Sun et al. |
| 6,893,406 B2 | 5/2005 | Takeuchi et al. |
| 6,897,788 B2 | 5/2005 | Khair et al. |
| 6,971,993 B2 | 12/2005 | Fletcher |
| 7,071,844 B1 | 7/2006 | Moise |
| 7,127,270 B2 | 10/2006 | Sinclair |
| 7,768,499 B2 | 8/2010 | Sturtz |
| 7,942,782 B2 | 5/2011 | Al-Tawil |
| 7,995,031 B2 | 8/2011 | Manal |
| 8,040,858 B2 | 10/2011 | Muhamed et al. |
| 8,044,766 B2 | 10/2011 | Ghovanloo et al. |
| 8,046,491 B2 | 10/2011 | Klein et al. |
| 8,047,964 B2 | 11/2011 | Al-Tawil |
| 2011/0057874 A1 | 3/2011 | Al-Tawil |
| 2011/0287392 A1 | 11/2011 | Al-Tawil |

OTHER PUBLICATIONS

Pressure Mapping Systems article, http://www.sensorland.com/HowPage033.html (May 22, 2008) (7 pages).

Pressure Transducers article, http://www.omega.com/prodinfo/pressuretransducers.html (May 27, 2008) (3 pages).

Piezoelectric Sensor article, http://en.wikipedia.org/wiki/Piezoelectric_sensor (May 27, 2008) (5 pages).

ASDX Sensors, brochure, www.honeywell, com/sensing (Sep. 28, 2009) (4 pages).

Adult Pacifier article, http://www.diaperconnection.com/pacifier.html (Sep. 28, 2009) (3 pages).

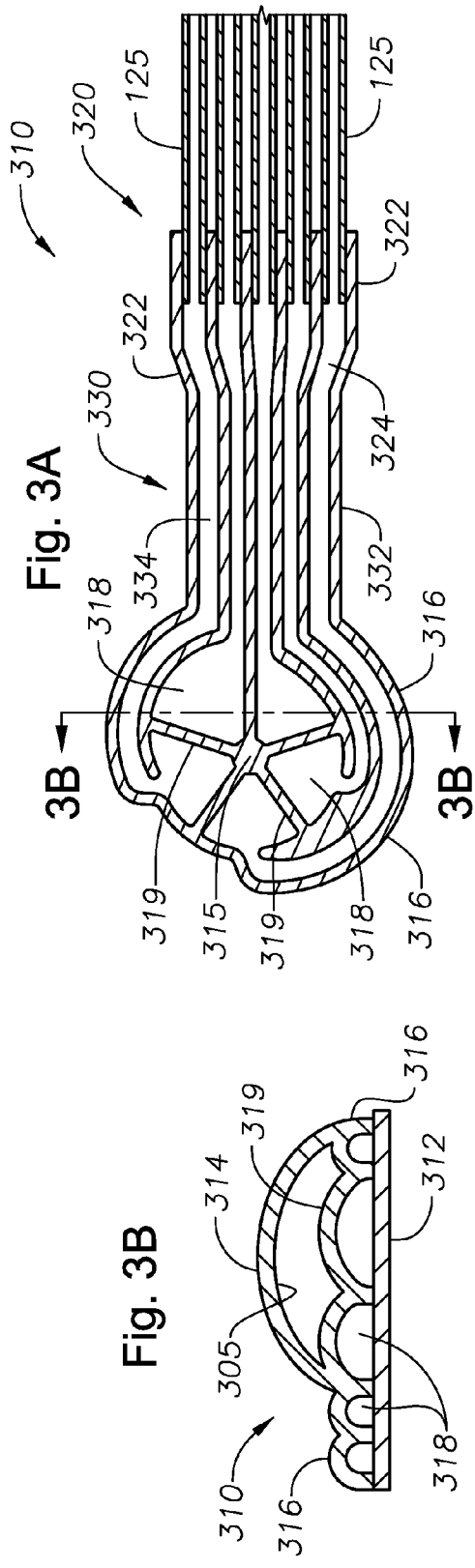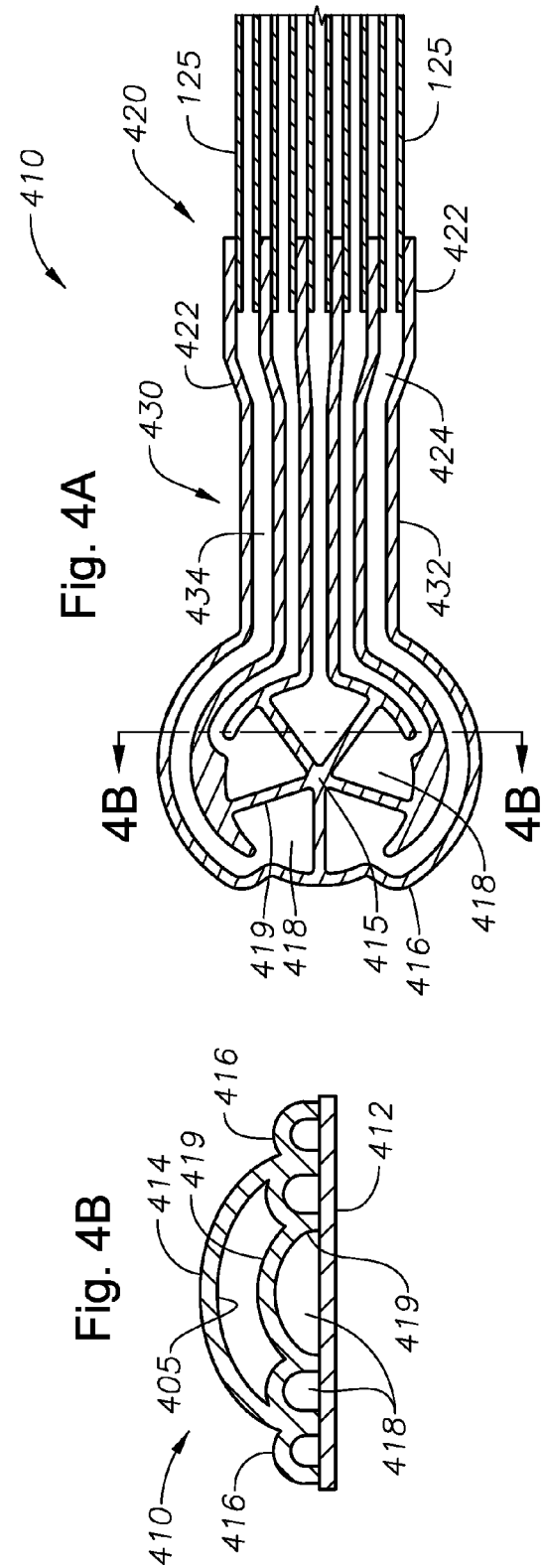

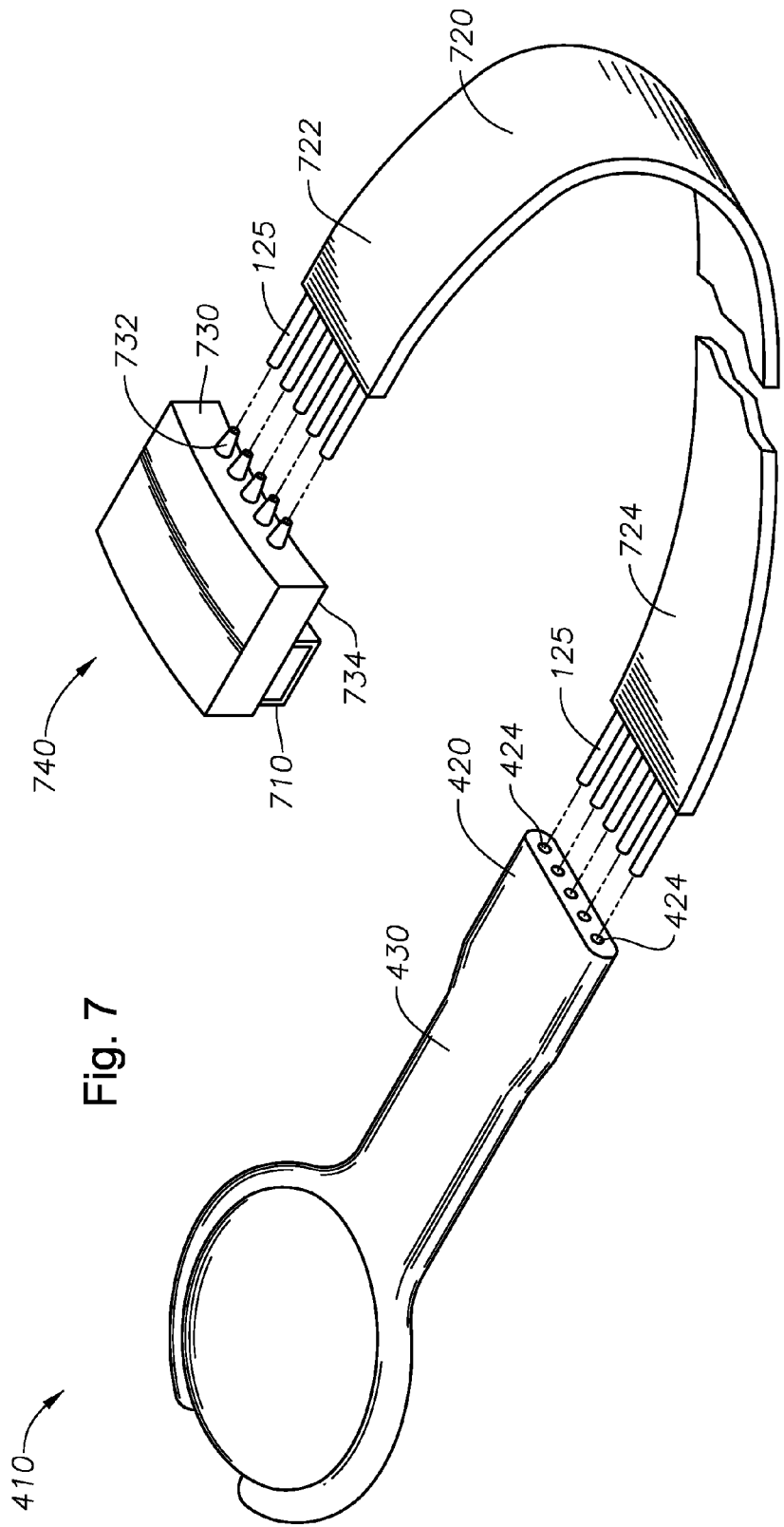

ns. U.S. Pat. No. 6,833,786 presents a pneumatic de-mul-
WIRELESS HEAD SET FOR LINGUAL MANIPULATION OF AN OBJECT, AND METHOD FOR MOVING A CURSOR ON A DISPLAY

CROSS REFERENCE TO RELATED APPLICATIONS

This application claims the benefit of a non-provisional patent application bearing U.S. Ser. No. 13/092,234 filed 22 Apr. 2011. That application is entitled "Head Set for Lingual Manipulation of an Object, and Method for Moving a Cursor on a Display."

The non-provisional application claimed the benefit of U.S. Ser. No. 12/782,356, filed 18 May 2010. That application is entitled "Methods and Systems for Lingual Movement to Manipulate an Object." This non-provisional application, in turn, claimed the benefit of U.S. Ser. No. 12/556,237, filed 9 Sep. 2009, also entitled "Methods and Systems for Lingual Movement to Manipulate an Object."

The '237 non-provisional patent application claimed the benefit of a provisional patent application bearing U.S. Ser. No. 61/096,508, filed 12 Sep. 2008.

These related applications are each incorporated herein by reference in their entireties.

STATEMENT REGARDING FEDERALLY SPONSORED RESEARCH OR DEVELOPMENT

Not applicable.

BACKGROUND OF THE INVENTION

1. Field of the Invention

The present invention relates to assistive devices. More specifically, the present invention relates to a head set that allows an individual who has limited use of their upper extremities to change the position or status of an object through lingual manipulation. The invention also relates to tongue-operated wireless communication devices.

2. Technology in the Field of the Invention

Some individuals have limited use of their upper extremities. Such individuals may, for example, have suffered a stroke. The term "stroke" is a lay term that refers to a condition wherein the blood supply to an area of the brain is temporarily cut off. When blood fails to get through to parts of the brain, the oxygen supply to those areas is cut off. Without oxygen, brain cells die. The longer the brain is without blood, the more severe the damage will be. Where the portion of the brain that controls movement of the upper extremities is damaged, the individual may be left in a state of partial paralysis.

Individuals may also lose function of their upper extremities as a result of an injury. Such injuries may occur due to a car accident, a diving accident, a fall, or other trauma. In these instances, the individual's cervical spine and nerves may be injured, producing partial or complete paralysis of the hands or arms.

In addition to these events, some individuals may develop upper paralysis as a result of a medical condition. Examples of such conditions include amyotrophic lateral sclerosis (ALS), hypokalemia periodic paralysis, cerebral palsy, or other diseases. Finally, some individuals may completely lose all or a portion of both arms due to an explosion or accident incident to work or military duty.

When any of these conditions of paralysis or injury occur, the individual is left without the ability to move an object using his or her arms. Thus, the individual cannot turn off a light, adjust a bed, change a channel, send text messages, or conduct countless other activities that most people take for granted.

Assistive devices have been presented for disabled persons. U.S. Pat. No. 6,833,786 presents a pneumatic de-multiplexer that utilizes a "sip-and-puff" tube for manipulating an appliance. The sip-and-puff technology allows a user to selectively inhale and exhale to cause movement of a wheelchair or to operate another appliance. However, sip-and-puff technology would be extremely cumbersome for typing a message on a display or for navigating web-based applications on a micro-computer.

U.S. Pat. No. 7,071,844 describes a wireless, tongue-operated device for controlling electronic systems. The device is said to utilize a single electrical sensor 11 embedded in an oral sensor-mounting device, such as a dental retainer or a mouthguard. The sensor is said to generate electrical signals to an interface, which then processes the signals into control signals. The '844 patent fails to identify a source, name, or model number for the depicted electrical sensor. Further, the '844 patent fails to describe how the sensor would be powered (neither a power wire nor a cable is shown or mentioned), and fails to explain where one would obtain or how one would design an electrical sensor offering multiple detected regions for computing movement of a user's tongue.

Therefore, a need exists for an improved apparatus that will allow an individual having limited use of their upper extremities to move or change the state of an object using their tongue. Further, a need exists for a head set having a connected mouthpiece that allows an individual to move a cursor on a display using lingual manipulation. Finally, a need exists for a head set that enables the typing of characters on a digital keyboard for the purpose of sending a text message or navigating a web site.

BRIEF SUMMARY OF THE INVENTION

A head set is first provided herein. The head set is beneficial for assisting an individual who is significantly impaired in the use of his or her upper extremities. The head set enables such an individual to manipulate an object. The object may be a mechanical device such as a door or a bed. Alternatively, the object may be an electrical appliance, wherein "moving" the appliance means turning it on, off, up or down. Alternatively still, the object may be a cursor on a digital display or screen.

In one embodiment, the head set first includes a head piece. The head piece preferably comprises a pair of opposing head rests joined together by an arched support member. Preferably, at least one of the head rests is adjustable relative to the support member.

The head set also includes an articulating arm. The articulating arm extends from a head rest, and has a distal end. In one aspect, the articulating arm comprises a first arm portion extending from one of the head rests, and a pivot point away from the head rest. The articulating arm then comprises a second arm portion connected to the pivot point, and having the distal end of the arm extending away from the pivot point.

The head set also includes a mouthpiece. The mouthpiece defines a bulb that is dimensioned to fit inside a user's mouth. The bulb is connected proximate the distal end of the articulating arm. The bulb is fabricated from an elastomeric material.

The mouthpiece has a plurality of cells embedded therein. The cells are configured to receive pressure applied by the tongue of an individual. In one embodiment, the mouthpiece comprises at least three outer cells, or alternatively, at least five cells, with the cells being disposed radially around the mouthpiece. The cells are separated by walls fabricated within the mouthpiece.

Each of the cells contains a fluid. The fluid may be air or some other non-toxic gas. In this instance, the cells may be referred to as air cells. Alternatively or in addition, the fluid may be water or other non-toxic liquid. In this case, the cells are fluid cells. For ease of reference, the cells will be described herein as simply that—cells.

The head set also includes a plurality of tubes. Each tube has a proximal end and a distal end. The distal end of each of the tubes is in substantially sealed fluid communication with a corresponding cell. This may be by means of an integral connection between the distal end of the tubes and respective walls. More preferably, the distal ends of the tubes are received in channels associated with the individual cells.

Each of the plurality of tubes may generally reside at ambient pressure. Alternatively, and by way of example only, each of the plurality of tubes may be pre-loaded at a pressure of about 15 psi to 25 psi.

A plurality of transducers is also provided as part of the head set. Each transducer is in substantially sealed fluid communication with the proximal end of a corresponding tube. The transducers convert changes in pressure within the respective cells to corresponding electrical signals. Such electrical signals may be, for example, voltage signals, current signals, or resistive changes. The transducers are preferably in the nature of pressure sensors.

The head set further includes a first processor. The first processor processes the electrical signals. The processor may include an analog-to-digital converter, meaning that electrical signals from the pressure sensors are converted into digital values. The converted electrical signals, such as voltage signals, are then modulated to generate a pressure profile from the cells. The pressure profile represents a magnitude of pressure within the cells, a direction of pressure, a duration of pressure, or combinations thereof. The processor converts the pressure profile into operational commands via software or firmware.

The operational commands are sent via a wireless transmitter that is also part of the head set. The transmitter delivers the commands to a transceiver. The transceiver is in electrical communication with a second processor. The second processor causes a cursor to move across a display, with the display having alphanumeric and/or other symbols. Thus, the first processor communicates wirelessly with the display via the second processor.

In this embodiment, the display provides a visual platform for the movement of a cursor in accordance with the pressure profile. The cursor is manipulated by application of pressure on the cells using lingual movement. Once the cursor is in position over a letter or other symbol, the user may "click" on the symbol.

In one embodiment, "clicking" a symbol activates a motor on an appliance or changes the state of an electrical appliance. For example, the transceiver may send instructions that cause the motor to move an object such as a bed, a door or a wheelchair. Alternatively, the transceiver may send an instruction to a switch. The switch changes the electrical state of an appliance such as a light fixture, a television, or a thermostat. Thus, the first processor is in operationally electrical communication with an electrical appliance or a switch.

In a preferred embodiment, the display includes a digital keyboard. Moving the cursor over the keyboard allows a user to "type" a message or "click" on a link to a web page or access an application. Thus, even a user with severe limitations to his or her upper extremities is able to use a micro-computer such as a tablet, a smart phone, or a personal digital assistant. The only requirement is that the micro-computer have wireless capability such as Wi-Fi, Wi-Max, or Bluetooth.

A method for moving a cursor using lingual manipulation is also provided herein. The method first includes providing a head set for a user. The head set is designed in accordance with the head set described above. In this respect, the head set has a head piece, and an articulating arm extending from the head piece. The articulating arm has a distal end.

The head set also includes a mouthpiece. The mouthpiece defines an elastomeric bulb that is connected proximate the distal end of the articulating arm. The bulb has a plurality of cells embedded therein for receiving pressure applied by the tongue of a user. The mouthpiece is dimensioned to fit inside the mouth of a user.

The head set also includes a plurality of tubes. Each tube has a proximal end and a distal end. The distal end of each of the tubes is in substantially sealed fluid communication with a corresponding cell. The head set then also includes a plurality of transducers. Each transducer is in substantially sealed fluid communication with the proximal end of a corresponding tube. The transducers convert changes in pressure within the respective cells to corresponding electrical signals. Such electrical signals may be, for example, voltage signals, current signals, or resistive changes. The transducers are preferably in the nature of pressure sensors.

The head set further includes a first processor. The first processor processes the electrical signals. The converted electrical signals, such as voltage signals, are then modulated to generate a pressure profile from the cells. The first processor resides on the head set and converts the pressure profile into operational commands via software or firmware.

The pressure profile is based upon pressure readings from the various cells. In one aspect, pressure signals are processed such that each electrical signal represents a pressure reading from a corresponding cell or from the combined cells. Electrical signals from one or more corresponding cells may be averaged over a specified period of time to produce the pressure profile. The pressure profile may be in, for example, vector form or matrix form. The pressure profile may have a peak indicative of location at which pressure is being generated within the one or more cells during the specified period of time.

The processor also includes a transmitter. The transmitter is part of the head set, and is configured to wirelessly communicate with a transceiver. In one aspect, the transmitter is an infrared controller. In another aspect, the transmitter is a first transceiver that uses Bluetooth, Wi-Fi, Zigby, or other wireless technology to send command signals that correspond to the pressure profile. The first transceiver communicates with a second transceiver that in turn communicates with a second processor. The second processor causes a cursor to move across a display in response to the command signals. Thus, the first processor communicates wirelessly with the display via the second processor.

The method also includes placing the plurality of tubes in fluid communication with the corresponding plurality of transducers. Manipulating air pressure within the plurality of tubes allows a user to cause the cursor on the display to move in accordance with the pressure profile.

Preferably, the method also includes providing one or more symbols on the display. The user may "click" on a symbol using the cursor as controlled by the user's tongue. The symbol on the display comprises a picture, one or more alphanumeric characters, an arrow, a geometric figure, or combinations thereof.

In one embodiment, the second processor is in electrical communication with a motor for moving an object. In this instance, one of the one or more symbols on the display corresponds to the object. The object may be, for example a bed, a wheelchair, or a door. The user may "click" on a symbol using the cursor and their tongue to, for example, cause a door to close or to cause a wheelchair to move.

Alternatively, the second processor is in electrical communication with an electrical appliance. In this instance, one of the one or more symbols on the display corresponds to the appliance. The appliance may be, for example, a light fixture, a television, or a thermostat. The user may "click" on a symbol using the cursor and their tongue to, for example, cause a light to dim or to turn on and off.

Preferably, the display presents a digital keyboard. This allows the user to move the cursor using lingual manipulation in order to select a series of characters on the keyboard. In this way, the user may compose a textual message or navigate web sites. The method then includes the step of providing a "send" symbol on the display that, when selected by the user, sends the textual message or a search command through a wireless communications system.

Finally, a method of typing characters on a virtual keyboard using lingual musculature is provided herein. In one embodiment, such method includes providing a head set as generally described above. The method further includes placing the plurality of tubes in fluid communication with the corresponding plurality of transducers. Preferably, each of the plurality of transducers is a pressure sensor having a diaphragm that is sensitive to changes in pressure within a corresponding tube. These changes are processed as electrical signals, and converted into command signals.

The method also includes sending the command signals to a transceiver, wherein the transceiver is in operative electrical communication with a display. The display includes a digital keyboard. A cursor on the display is caused to move in accordance with the pressure profile. The cursor is used to select characters on the virtual keyboard. The selected characters on the virtual keyboard are "clicked" using the mouthpiece. In this way, the user may compose a textual message one character at a time. Alternatively, the user may click on a link in to a web page or operate an application on a tablet or conduct an internet search.

BRIEF DESCRIPTION OF THE DRAWINGS

So that the manner in which the present invention can be better understood, certain illustrations, charts and/or flow charts are appended hereto. It is to be noted, however, that the drawings illustrate only selected embodiments of the inventions and are therefore not to be considered limiting of scope, for the inventions may admit to other equally effective embodiments and applications.

FIG. 3A is a top, cross-sectional view of a mouthpiece as may be used with a head set of the present inventions, in an alternate embodiment.

FIG. 3B is a cross-sectional view of the mouthpiece of FIG. 3A, taken across line 3B-3B.

FIG. 4A is a top, cross-sectional view of a mouthpiece as may be used with a head set of the present inventions, in yet another alternate embodiment.

FIG. 4B is a cross-sectional view of the mouthpiece of FIG. 4A, taken across line 4B-4B.

FIG. 7 is an enlarged perspective view of a tube bundle in an alternative embodiment. A mouthpiece is seen at one end of the tube bundle, and an electronics box for containing operational components is shown at an opposite end of the tube bundle.

In FIG. 8A, the display shows a cursor that may be moved on a display. The cursor is moved through lingual manipulation in order to operate a wheelchair or other mechanical device.

In FIG. 8B, the display also shows a cursor that may be moved on a display. Here, the cursor is moved through lingual manipulation in order to change the status of an electrical appliance.

In FIG. 8C, the display again shows a cursor that may be moved on a display. Here, the cursor is moved through lingual manipulation in order to "press" or "click" on keys from a virtual keyboard.

DETAILED DESCRIPTION OF CERTAIN EMBODIMENTS

Definitions

As used herein, the term "cursor" means any indicator of a position on a computer screen or display. The cursor may be, for example, a flashing bar, an underline, or an arrow or other symbol.

The term "send" refers to any hey or any action for activating an electronic action. Such actions may include performing a search, sending a query, or sending a text message or an e-mail.

The term "first processor" means any device that has a computational element in communication with a transmitter. The first processor may be a microprocessor, a microcontroller, a complex instruction set computing (CISC) microprocessor, a reduced instruction set (RISC) microprocessor, a very long instruction word (VLIW) microprocessor, or any other type of processor or processing circuit that may be embedded in an electrical circuit board for communicating with pressure transducers.

The term "second processor" means any device that is separate from the "first processor" but that also has a computational element. The second processor may be a microprocessor, a microcontroller, a complex instruction set computing (CISC) microprocessor, a reduced instruction set (RISC) microprocessor, a very long instruction word (VLIW) microprocessor, or any other type of processor or processing circuit found within a personal digital assistant or a tablet. The second processor may be a personal digital assistant; alternatively, the second processor may be a part of a laptop computer or a desktop computer.

The term "tablet" means any portable electronic device having a transceiver that allows a user to read a book, view a video, download a song, send a text message, view an e-mail message, manage a calendar, maintain a personal directory, or combinations thereof.

The term "personal digital assistant" refers to any hand-held computer having wireless communication capability. An example is a so-called "smart phone," such as a Blackberry®, a Droid®, or an iPhone®.

The term "transmitter" includes any device or protocol for sending a wireless signal. The transmitter may be an infrared controller or other device that provides essentially one-way instructions or commands. Alternatively, the transmitter may be a transceiver that uses a two-way communications protocol. In this instance, the transmitter may utilize, for example, Bluetooth technology.

DESCRIPTION OF SPECIFIC EMBODIMENTS

Figure 1:
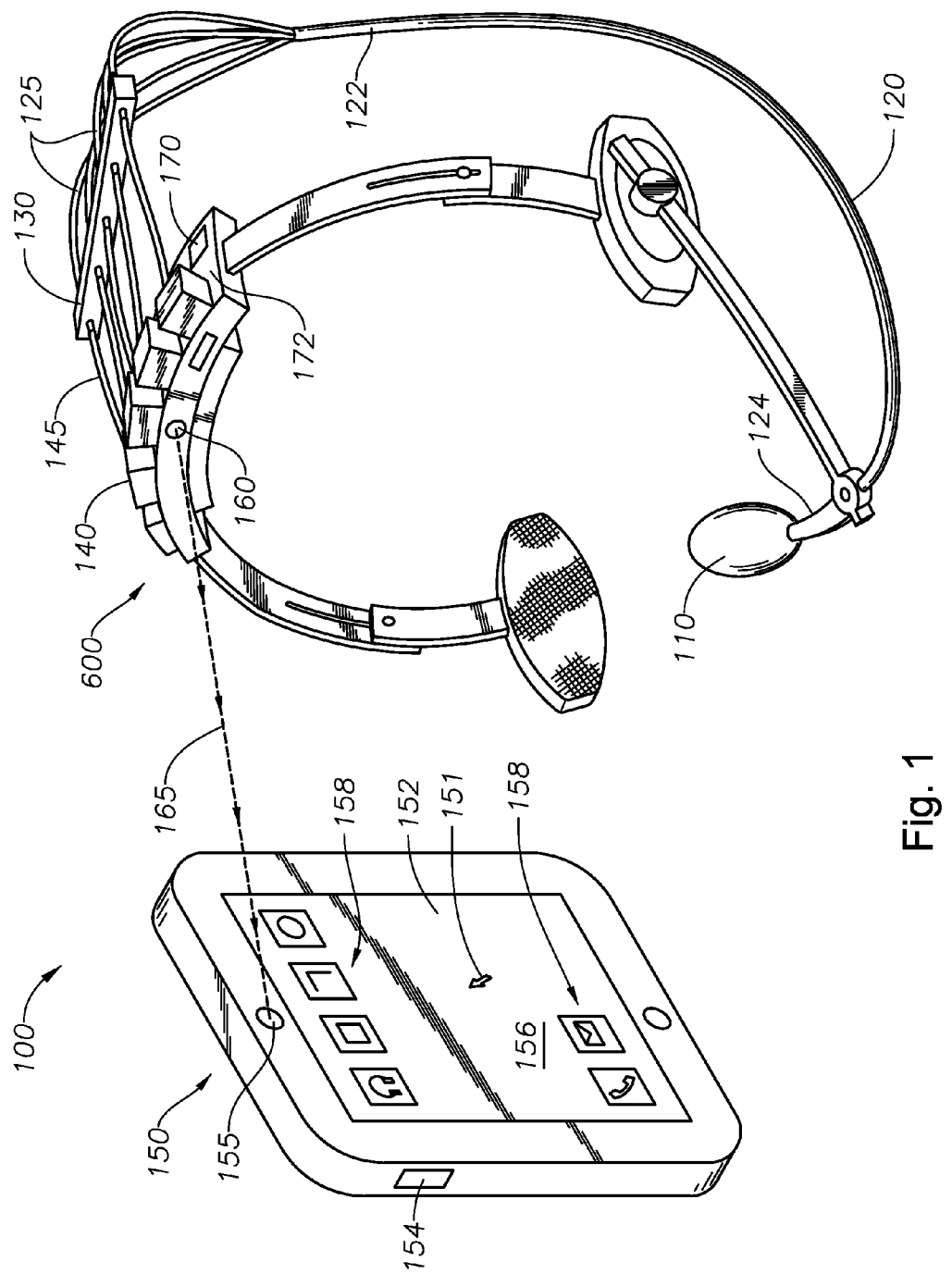
FIG. 1 is a perspective view of an intra-oral system according to the present invention, in one embodiment. A head set is seen as part of the system, with the head set having a bulbous mouthpiece.

FIG. 1 is a perspective view of an intra-oral system 100, in one embodiment. Various components of the system 100 are shown. The system 100 generally includes a mouth piece 110, a head set 600 for supporting the mouth piece 110, a first processor 172 located on the head set 600, and a second processor 150. As will be described more fully below, the first processor 170 is preferably a micro-controller, while the second processor 150 is preferably a micro-computer, such as a so-called tablet or a so-called personal digital assistant.

The purpose of the intra-oral system 100 is to allow a user who has limited use of his or her upper extremities to communicate with the processing unit 150. More specifically, the head set 600 allows the user to communicate with the processing unit 150 for the purpose of sending and receiving text messages, for navigating web sites and dedicated applications, for reading a book, for changing the status of an appliance, or combinations thereof. The head set 600 is mechanically untethered to the second processor 150 and any appliances that it may operate.

The intra-oral system 100 operates by means of a mouth piece 110. The mouth piece 110 may be referred to as a "mouth mouse," as it allows the user to move a curser on a computer display using lingual musculature. In FIG. 1, an illustrative display is shown at 156.

Figure 2A:
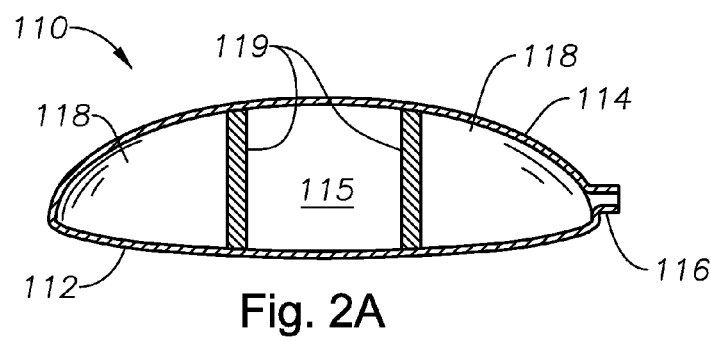
FIG. 2A is a cross-sectional view of the mouthpiece from the intra-oral system of FIG. 1, in one embodiment. The cross-section is taken across a major axis of the mouthpiece.
Figure 2B:
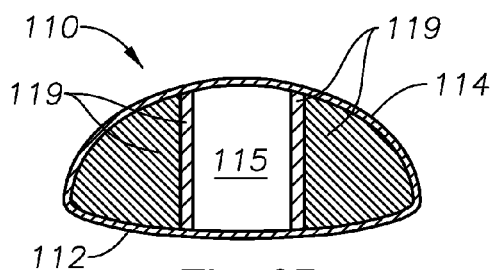
FIG. 2B is another cross-sectional view of the mouthpiece from the system of FIG. 1. Here, the cross-section is taken across a minor axis of the mouthpiece.
Figure 2C:
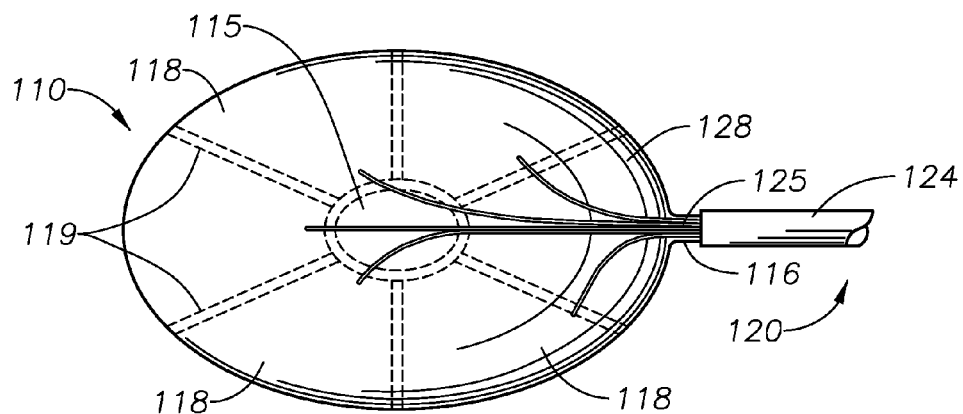
FIG. 2C is a top view of the mouthpiece from the system of FIG. 1. Individual fluid cells are shown along with corresponding tubes.

Enlarged views of the mouthpiece 110 are provided in FIGS. 2A through 2C. FIG. 2A is a cross-sectional view of the mouthpiece 110 from the system of FIG. 1 and the head set 600, in one embodiment. The cross-section is taken across a major axis. FIG. 2B is another cross-sectional view of the mouthpiece 110. Here, the cross-section is taken across a minor axis. FIG. 2C is a top view of the mouthpiece 110 from the head set 600. Features of the mouthpiece 110 will be discussed with reference to these three figures together.

The mouthpiece 110 is designed to be substantially hollow. To this end, the mouthpiece 110 defines a bottom surface 112 and a top surface 114. The bottom surface 112 is preferably substantially flat while the top surface 114 is preferably curved, or convex, to create an arcuate profile. The arcuate profile is designed to conform to the concave shape of a user's mouth.

The mouthpiece 110 is configured to be selectively inserted into an individual's mouth (not shown). As noted, the individual is preferably a person who has limited use of their upper extremities. However, the individual may also be may be a patient who is in need of therapy to develop the intra-oral musculature. Such a patient may be, for example, a stroke victim or the victim of a head or neck injury. Alternatively, such a patient may be a child who suffers from congenital limitations in chewing and/or swallowing food.

The mouthpiece is preferably fabricated from an elastomeric material. Suitable materials may include polyisoprene rubber, chloroprene rubber, neoprene rubber, styrene butadiene rubber, and acrylonitrile butadiene rubber. Additional suitable examples include silicone, ethylene propylene diene methylene, polyvinylchloride, polyethylene, polyurethane, urethane-coated nylon, and ethyl vinyl acetate. Combinations of these materials may also be employed.

The mouthpiece 110 includes a plurality of cells 115, 118. In the arrangement of FIGS. 2A through 2C, six cells 115, 118 are provided. These represent a central cell 115 and then five separate cells 118 spaced radially around the central cell 115. Preferably, at least three radial cells 118 are used. In the illustrative arrangement of FIGS. 2A through 2C, the mouthpiece 110 has five radial cells 118. The radial cells 118 preferably are equi-radial in dimension, meaning that each cell 118 forms a substantially equal angle extending from a center point of the mouthpiece 110. In addition, each radial cell 118 has a substantially similar volume.

Each cell 115, 118 holds a volume of fluid. The fluid may be a compressible fluid, or gas. The compressible fluid may be air or another non-toxic gas. The compressible fluid may comprise oxygen, carbon dioxide, nitrogen, helium, argon, or combinations thereof. Alternatively, the fluid may be a substantially non-compressible fluid, such as water or other non-toxic liquid. A combination of compressible and non-compressible fluids may also be employed. In any instance, fabrication of the intra-oral system 100 will typically involve establishing a baseline pressure within the cells 115, 118, as discussed more fully below.

Preferably, the fluid is held at ambient pressure. Alternatively, the fluid in the cells 115, 118 is pre-loaded at a higher pressure such as between about 15 psi and 25 psi. In this way, the mouthpiece 110 is at least nominally resistive to pressure placed by the patient using his or her tongue.

To define the cells 115, 118, the mouthpiece 110 includes a series of walls 119. The walls 119 are sealed between the bottom surface 112 and the top surface 114. Sealing may be through heat sealing, RF sealing, or other mechanisms known in the art of plastic injection molding or other molding techniques.

The cells 118 of the mouthpiece 110 are in fluid communication with respective tubes 125. The tubes 125 are seen in the top view of FIG. 2C. Each cell 118 receives its own tube 125. It is noted that in the arrangement of FIG. 2C, the central cell 115 does not receive a tube, but is dead. Indeed, in one arrangement, the central cell 115 may hold no fluid, but just defines a center point in the mouthpiece 110.

The tubes 125 are sealingly disposed within the walls 119 of the mouthpiece 110. The tubes 125 are preferably manufactured to be integral to respective walls 119.

The mouthpiece 110 and the connection to the tubes 125 may be configured in different sizes. The size will primarily be dictated by the size of the individual user's mouth. It is noted that for smaller users, fewer cells may be necessitated due to size limitations. The number of cells will affect the manner in which the intra-oral system 100 is programmed.

The tubes 125 exit the mouthpiece 110 through an end opening 116. The end opening 116 defines a circular orifice that frictionally and, optionally, sealingly receives a bundle of tubes 125. The tubes 125 extend from respective walls 119, travel through an end area 128 of the mouthpiece 110 (which is preferably not a cell), travel through the end opening 116, and then exit the mouthpiece 110.

In the mouthpiece 110 of FIG. 2C, the tubes 125 connect to the walls 119 internal to the mouthpiece 110, that is, through the end area 128 and through the central cell 115. However, some or all of the tubes 125 may alternatively enter the cells 115 from a top, a bottom or an outer edge of the bulb defining the mouthpiece 110. The present inventions are not limited by the method of providing fluid communication between the tubes 125 and the cells 115 unless so provided in the claims.

In the arrangement of FIGS. 1 and 2C, the tubes 125 are optionally bundled as they exit the mouthpiece 110. That means that the tubes 125 are held together externally by a tubular sheath 120. The tubular sheath 120 protects the individual tubes 125, and also prevents them from becoming tangled en route to the head set 600.

The mouthpiece and tubes arrangement of FIGS. 2A through 2C is merely illustrative. Other arrangements for the mouth piece 110 and tubes 125 may be provided. Alternate arrangements are shown in FIGS. 3A through 3B, and FIGS. 4A through 4B.

First, FIG. 3A is a top, cross-sectional view of a mouthpiece 310 as may be used in the intra-oral system 100 of FIG. 1, in an alternate embodiment. FIG. 3B is a cross-sectional view of the mouthpiece 310 of FIG. 3A, taken across line 3-3. The mouthpiece 310 provides an eccentric cell design. The mouthpiece 310 will be described with reference to FIGS. 3A and 3B, together.

The mouthpiece 310 first includes a plurality of cells 318. The cells 318 are defined by walls 319 that form the cells 318. As shown in the cross-sectional view of FIG. 3B, the walls 319 are sealed with a bottom surface 312. However, portions of the walls 319 are separate from a top surface 314.

The bottom surface 112 is preferably substantially flat, while the top surface 114 is preferably curved, or convex, to create an arcuate profile. The arcuate profile is designed to conform to the concave shape of a user's mouth. The top surface 314 over-arches several of the cells 318 in an eccentric fashion. In doing so, the top surface 314 forms a partially-hollow bulb 305.

The cells 318 are radially disposed about a centerpoint 315. In the arrangement of FIG. 3A, the centerpoint 315 is not the geometric center of the bulb 305. The cells 318 are also encompassed by an outer wall 316. The outer wall 316 is preferably integral to the bottom surface 312 and the top surface 314.

The bulb 305 is located at a proximal end 340 of the mouthpiece 310. The mouthpiece 310 also has a distal end 320 where a connection to the tubes 125 is made. This means that the mouthpiece 310 connects to the tubes 125 outside of the user's mouth. The distal end 320 is opposite from the bulb 305.

The distal end 320 has a series of walls 322. The walls 322 form five channels 324. Each channel 324 is configured to sealingly receive a respective tube 125. Intermediate the proximal end 340 and the distal end 320 is a transition section 330. The transition section 330 also includes walls 332 that form five channels 334. The transition channels 334 place the tubes 125 in fluid communication with respective cells 318.

Second, FIG. 4A provides a top, cross-sectional view of a mouthpiece 410 as may be used in the intra-oral system 100 of FIG. 1, in yet another alternate embodiment. FIG. 4B is a cross-sectional view of the mouthpiece 410 of FIG. 4A, taken across line 4-4. Here, the mouthpiece 410 provides a concentric cell design. The mouthpiece 410 will be described with reference to FIGS. 4A and 4B, together.

As with mouthpiece 310, the mouthpiece 410 first includes a plurality of cells 418. The cells 418 are defined by walls 419 that form the cells 418. As shown in the cross-sectional view of FIG. 3B, the walls 419 are sealed with a bottom surface 412. However, portions of the walls 419 are separate from a top surface 414.

The bottom surface 412 is preferably substantially flat, while the top surface 414 is preferably curved, or convex, to create an arcuate profile. The arcuate profile is designed to conform to the concave shape of a user's mouth. The top surface 414 over-arches several of the cells 418 in a concentric fashion. In doing so, the top surface 414 forms a partially-hollow bulb 405.

The cells 418 are radially disposed about a centerpoint 415. In the arrangement of FIG. 4A, the centerpoint 415 is near the geometric center of the bulb 405. The cells 418 are also encompassed by an outer wall 416. The outer wall 416 is preferably integral to the bottom surface 412 and the top surface 414.

The bulb 405 is located at a proximal end 440 of the mouthpiece 410. The mouthpiece 410 also has a distal end 420 where a connection to the tubes 125 is made. This means that the mouthpiece 410 again connects to the tubes 125 outside of the user's mouth. The distal end 420 is opposite from the bulb 405.

The distal end 420 has a series of walls 422. The walls 422 form five channels 424. Each channel 424 is configured to sealingly receive a respective tube 125. Intermediate the proximal end 440 and the distal end 420 is a transition section 430. The transition section 430 also includes walls 432 that form five channels 434. The transition channels 434 place the tubes 125 in fluid communication with respective cells 418.

It is noted that in each mouthpiece 310, 410, each cell (318 or 418) and its corresponding channel (334 or 434) forms a volume for holding fluid. The cells and corresponding channels preferably have substantially similar volumes. However, this is not critical, as the cells 318, 418 and corresponding channels 334, 434 may be pre-loaded with fluid so as to equalize pressures among the cells 318, 418.

Figure 5:
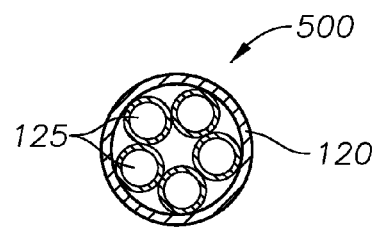
FIG. 5 is a cross-sectional view of the tube bundle associated with the head set of FIG. 1, in one embodiment.

Regardless of the mouthpiece arrangement, fluid pressure is delivered from the mouthpiece to the individual tubes 125. The tubes 125 are bundled into a sheath 120. FIG. 5 is a cross-sectional view of a tube bundle 500 from the system 100, in one embodiment. In the arrangement of FIG. 5, the tube bundle 500 includes a tubular sheath 120. The tubular sheath 120 helps to protect the tubes 125 and keeps them from getting punctured or tangled. Five illustrative tubes 125 are seen within the tubular sheath 120. Each tube 125 defines a channel through which fluid passes. It is understood that any number of tubes 125 and corresponding cells (such as 115, 118) may be used in the system 100.

Figure 6:
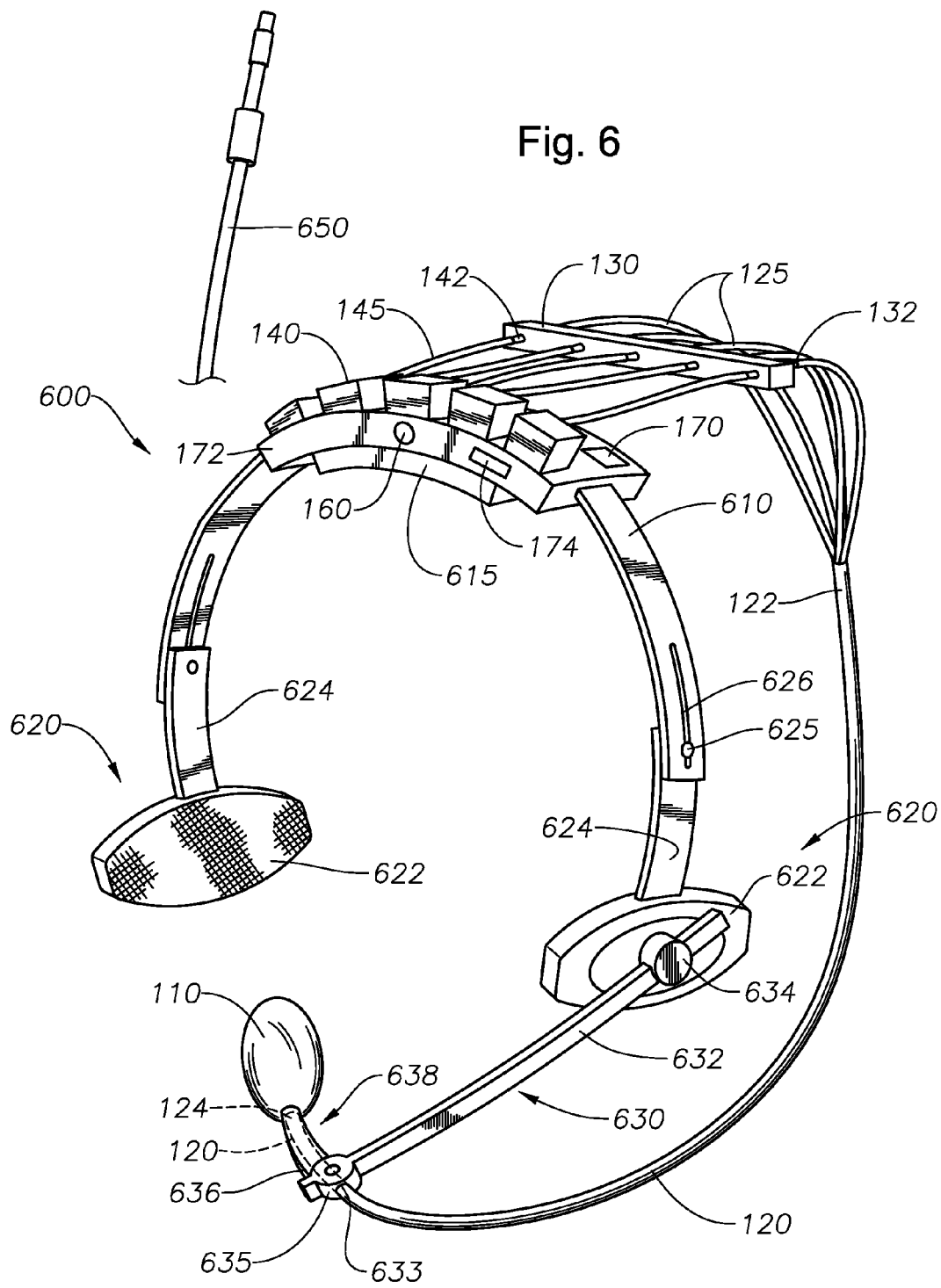
FIG. 6 is an enlarged perspective view of the head set of the present inventions, in one embodiment.

In the intra-oral system 100, the tubes 125 are connected to the head set 600. FIG. 6 is an enlarged perspective view of the head set 600 of the present invention, in one embodiment. Here, the head set 600 is shown apart from the intra-oral system 100.

The head set 600 is designed and configured to be worn on the head (not shown) of a user. The user is preferably an individual who has lost function of at least their hands and, possibly, additional portions of their upper extremities. However, the head set 600 may be worn by any individual.

The head set 600 first includes a support member 610. The support member 610 defines an arcuate or arched member configured to rest on the crown of an individual user's head. The support member 610 optionally includes a central cushioning member 615.

The head set 600 also includes opposing head rests 620. In the arrangement of FIG. 6, the head rests 600 each include pads 622 and supporting bars 624. The supporting bars 624 include pins 625. The pins 625 slidably move through slots 626 in the arcuate support member 610. In this way, one or both of the head rests 620 is adjustable relative to the head set 600.

The head set 600 also includes an articulating arm 630. In the arrangement of FIG. 6, the articulating arm 630 has a first arm portion 632 and a second arm portion 636. The first arm portion 632 has a proximal end 634 slidably and pivotally connected to one of the pads 622. The first arm portion 632 also has a pivot point 635 opposite the proximal end 634.

The second arm portion 636 pivots from the pivot point 635 of the first arm portion 632. Opposite the pivot point 635, the second arm portion 636 has a distal end 638. The mouthpiece 110 is connected to the articulating arm 630 at the distal end 638. In addition, the tubular sheath 120 is preferably supported by the second arm portion 636 as it extends away from the mouthpiece 110. Optionally, an opening 633 is provided in the first arm portion 632 or the pivot point 635 for receiving the tubular sheath 120. The second arm portion 636 may then be tubular, so as to guide the tubular sheath to the mouthpiece 110.

The unique head set 600 of the present inventions also includes a plurality of transducers 140. In the arrangement of FIG. 6, the transducers 140 are supported by the support member 610 in a linear array. Each transducer 140 is in fluid communication with an individual air tube 125.

The transducers 140 are in the nature of pressure sensors. The transducers 140 may be, for example, ASDX pressure sensors made by the Sensing and Control Division of Honeywell in Golden Valley, Minn. The ASDX series of pressure sensors utilize a small internal diaphragm for sensing fine variations in pressure. Different sensors are offered in the series for sensing within different pressure ranges. Such ranges include 0 to 1 psi, 0 to 5 psi, 0 to 15 psi, and 0 to 30 psi. The ASDX sensors offer a high level output (5.0 Vdc span) that is fully calibrated and temperature compensated with on-board Application Specific Integrated Circuitry (ASIC).

In the view of FIG. 6, the transducers 140 are resting over an electrical circuit board 172. The electrical circuit board 172 includes a first processor 170. Preferably, the first processor 170 is a micro-controller. The micro-controller 170 may be, for example, an Atmel® AVR® 8-bit microcontroller, useful for C and assembly programming. As another example, the micro-controller 170 may be the Atmel® 8-bit AVR RISC-based micro-controller that combines 16 KB ISP flash memory, 1 KB SRAM, 512B EEPROM, and an 8-channel/10-bit A/D converter (TQFP and QFN/MLF). The device supports a throughput of 20 MIPS at 20 MHz and operates between 2.7 and 5.5 volts.

A power switch 174 is also provided on the head set 600. The power switch 174 is associated with the electronics of the electrical circuit board 172. It is understood that the electronics will include an analog-to-digital ("ADC") converter for converting analog signals from the transducers 140 into digital signals for the micro-controller 170. The ADC converter may be integral to the transducers 140, or may be separate. The electronics may optionally also include a battery (not shown).

It is preferred that the transducers 140, the electrical circuit board 172 and the micro-controller 170 be housed within an electronics box. An electronics box is not shown in FIG. 1 or 6 so that components of the intra-oral system 100 may be more clearly seen. However, an illustrative electronics box is shown at 740 in FIG. 7, discussed below. The box 740 will have walls that protect the transducers 140, the micro-controller 170, and the printed circuit board 172.

The tubes 125 may connect directly from the mouthpiece 110 to the transducers 140. More preferably, the tubes 125 connect from the mouthpiece 110 to a manifold 130. The manifold 130 is preferably integral to the electronics box, as shown in the arrangement at 730 of FIG. 7.

Returning to FIG. 6, the manifold 130 includes a first array of nozzles 132 on the mouthpiece 110 side, and second array of nozzles 142 on the transducer 140 side. The tubes 125 are received over respective nozzles 132 external to the electronics box 740. In order to place the tubes 125 in fluid communication with the transducers 140, jumper tubes 145 are provided inside of the electronics box 740 between the nozzles 142 and the transducers 140.

The manifold 130 provides fluid channels (not shown) between the nozzles 142, 132 so that tubes 125 are in fluid communication with tubes 145. In this way, pairs of nozzles 142, 132 enable fluid communication through the tubes 125, 145 without necessity of the operator opening the box 740 and exposing the delicate transducers 140 and micro-controller 170. Further, the therapist or other operator is not required to manipulate the fragile connections between the jumper tubes 145 and the respective transducers 140. Preferably, the mouthpiece tubes 125 are color-coded with the array of nozzles 132 on the mouthpiece 110 side so that the tubes 125 properly correspond to the correct jumper tubes 145 and transducers 140. Alternatively, other coding systems may be used such as alphabetical or numeric associations, or the use of symbols. Alternatively still, custom connectors which connect the tubes 125 to the nozzles 132 in only one orientation may be utilized.

The jumper tubes 145, mouthpiece tubes 125 and manifold 130 place the transducers 140 in fluid communication with respective cells, such as cells 118. The manifold 130 creates five separate tubes by joining pairs of tubes 145, 125. A proximal end of each of the five tubes 145/125 is connected to a transducer 140, while a distal end of each of the five tubes 145/125 is connected to a respective cell 118 in the mouthpiece 110.

It is noted again that the tubes 125 are preferably bundled by a tubular sheath 120. A proximal end 122 of the tubular sheath 120 begins near the manifold 130, while a distal end 124 of the tubular sheath 120 extends towards the mouthpiece 110. In this way, the mouthpiece 110, the tubes 125 outside of the electronics box 740, and the tubular sheath 120 are essentially one integral unit. Each patient is supplied with his or her own mouthpiece 110 having integrated tubes 125 and the tubular sheath 120. The only "assembly" required by the therapist is to (i) optionally, "thread" the tubular sheath 125 through the second arm portion 636, and (ii) connect the tubes 125 with the external nozzles 132 on the manifold 130.

The transducers 140 are designed to convert changes in pressure within the cells 118 to electrical signals. The electrical signals may be raw analog voltage signals. Other examples of electrical signals that may be used include current signals or resistive changes. The changes in pressure within the cells 118 (and, optionally, 115) are delivered pneumatically or fluidically, depending on the fluid used, to the transducers 140 through the respective tubes 125. As the transducers 140 sense an increase in pressure, a corresponding voltage or other electrical signal is delivered through the electrical circuit board 172.

The micro-controller 170 uses operational software for processing the electrical signals. The electrical signals are delivered to the micro-controller 170 by means of the electrical circuit board 172. Of interest, the micro-controller 170 resides on and is mechanically supported by the head set 600 itself. The electrical signals, such as voltage signals, are then interpreted to generate a pressure profile from the cells, such as cells 118, 318 or 418. The pressure profile represents a magnitude of pressure from within the cells. Alternatively or in addition, the pressure profile represents a location or direction of pressure within the cells. Alternatively or in addition, the pressure profile represents a duration of pressure applied to the cells.

The pressure profile is based upon pressure readings from the various cells, either individually or through some combination. In one aspect, pressure signals are processed such that each electrical signal represents a pressure reading from a corresponding cell. Electrical signals from one or more corresponding cells may be averaged over a specified period of time to produce the pressure profile. The pressure profile has a peak indicative of location at which pressure is being generated within the one or more cells during the specified period of time.

The pressure profile can be used to determine direction. A curve-fitting technique may be used to determine the peak pressure, yielding a representation of the radial direction from 0 to 360 degrees. A windowed statistical analysis approach may also be employed for highly accurate measurements.

The pressure profile can be used to determine the magnitude of pressure applied by the patient. The preferred method is to use the average value of the pressure profile across all cells (such as cells 118, 318, or 418) to represent this magnitude in vector form. In certain scenarios, the associated pressure value from a central fluid cell 115 can be solely used to determine the magnitude. A baseline or steady-state value representing no pressure being applied to the mouthpiece 110 may be subtracted from the pressure profile to more accurately determine the actual pressure applied by the patient.

When a pressure profile is generated, a normalization procedure may be used to remove differences in pressure-to-voltage characteristics between cells. These differences can arise due to manufacturing imperfections in the cells and/or the electronics. Differences can also arise due to incidental variations in fluid volume within the cells, or incidental differences in volume size between the cells and associated tubes 125. The normalization values can be stored on the processor 170.

As noted, it may also be desirable to pre-load the cells and associated tubes 125 with a small amount of air pressure for purposes of calibration. This establishes a more accurate conversion of pressure changes to electrical signals by the transducers 140. This may be done, for example, by inserting air into or releasing air from the tubes 125 through a one-way valve (not shown).

Where a battery is not used, an electrical cord 650 extends from the head set 600. The cord 650 connects to a power pack (not shown), that may then plug into an electrical outlet for power. Alternatively, the electrical cord 650 has a USB connector (not shown) for placing the processor 170 and other electronics in electrical communication with a computer, such as a lap top (not shown).

It is preferred that the head set 600 be able to communicate with a second processor 150 through a wireless communication. Accordingly, the head set 600 also includes a transmitter 160. The transmitter 160 communicates with the second processor using an infrared controller. Alternatively, the transmitter 160 is a transceiver that communicates with the second processor using an RF signal, or by using other wireless means such as Bluetooth, Wi-Fi, Zigby, or Wi-Max.

Referring back to FIG. 1, a second processor 150 is shown. In the intra-oral system 100, the second processor 150 is a micro-computer such as a tablet or a personal digital assistant. The tablet may be, for example, an iPad®. The personal digital assistant may be, for example, a Droid®, a Blackberry® or an iPhone®. The second processor 150 includes a housing 152, a power switch 154, and a display 156. The second processor 150 also includes a cursor 151 and a plurality of icons 158. The icons 158 are indicative of programs or applications that may be run using the second processor 150. These programs may include text messaging, contacts storage, calendaring, photo storage, note keeping, and on-line game-playing. The icons 158 may also provide access to such programs as iTunes®, iPod®, YouTube®, Google Earth®, Google Mail®, Safari®, and a host of other well-known on-line applications. The icons 158 may also provide access to retail-based applications such as Starbucks®, Amazon®, e-Bay®, Target®, and so forth.

While the second processor 150 in FIG. 1 is a tablet or a personal digital assistant, it is understood that the second processor 150 may alternatively be a general purpose computer, such as a desk top computer or a laptop computer. What matters is that the second processor 150 also include a transceiver 155. The transceiver 155 receives wireless signals 165 from the transmitter 160 associated with the head set 600. The transceiver 155 may be, for example, an RF receiver. In either instance, communications software may be loaded onto the second processor 150 by the therapist or IT representative or field representative. However, the second processor 150 may be a specially designed or dedicated unit that comes with the head set 600.

In operation, the system 100 allows a patient to manipulate the cursor 151 on the display 156. This is done by the patient moving his or her tongue across and against the bottom surface 112 of the mouthpiece 110, 310, 410. Such movement causes an increase in pressure within selected cells 118 (or 318 or 418). The increase in pressure causes a corresponding increase in pressure within the tubes 125. The pressure changes, in turn, are transmitted to the respective transducers 140 on the head set 600.

Electrical signals are generated by the transducers 140 in response to the changes in pressure within the tubes 125. These signals are sent to the first processor 170. The processor 170, in turn, modulates the signals to determine tongue pressure values and locations. The processor 170 also recognizes tongue clicks. The process signals are then sent wirelessly to a second processor 150. The second processor 150 delivers motion commands to a cursor 151 using display software residing on the second processor 150. The cursor 151 is then caused to be moved across the display 156. Manipulation of the cursor allows the user to navigate programs and applications 158 associated with the second processor 150. Alternatively or in addition, the user may cause an external appliance to change its state.

The head set 600 and tubular sheath 120 present one arrangement for allowing a user to pneumatically send signals to a cursor 151. Other arrangements may be used though.

FIG. 7 is an enlarged perspective view of a tube bundle 720 provided between a mouthpiece and electronics. The tube bundle 720 provides an alternative to the tube bundle 500 of FIG. 5. Here, the tube bundle 720 is in the form of a ribbon cable. The tube bundle 720 is ideally suited for bundling air tubes 125 used with the mouthpieces 310 and 410. In the arrangement of FIG. 7, a mouthpiece is shown in perspective view. The illustrative mouthpiece is the mouthpiece 410 of FIG. 4.

The tube bundle 720 has a proximal end 722 and a distal end 724. In the view of FIG. 7, each end 722, 724 is loose. This means that individual air tubes 125 are exposed at the opposing ends 722, 724 of the tube bundle 720. The tube bundle 720 is beneficially designed to be a stand-alone part that may be selectively connected and un-connected to an electronics box 740 at the proximal end 722, and to the mouthpiece 410 at the distal end 724.

The mouthpiece 410 is shown in perspective view. The distal end 420 and the transition section 430 of the mouthpiece 410 are seen. In addition, channels 424 at the distal end 420 are visible. The channels 424 are dimensioned to slideably receive the fluid tubes 125 at the distal end 724 of the tube bundle 420.

FIG. 7 also shows an illustrative electronics box 740. The electronics box 740 is designed to house components of the head set 600, including the transducers 140, the jumper tubes 145, the electrical circuit board 172, the micro-controller (or first processor) 170, and the transmitter 160. A wall of the electronics box 740 serves as a manifold 730. The manifold 730 includes a plurality of nozzles 732. The manifold 730 further includes nozzles (not seen) on the transducer side, such as nozzles 142 from FIG. 6. The nozzles 142 place the transducers 140 in fluid communication with the air tubes 125 via jumper tubes 145 (seen in FIG. 1).

The electronics box 740 has a bottom surface 734. The bottom surface 734 includes a sleeve 710. The sleeve 710 is configured to receive the support member 610 from the head set 600. Cushions, seen at 615 in FIG. 6, may reside below the sleeve 710 to provide padding over the crown of a user's head.

The mouthpiece 410, the air tubes 125, the air tube bundle 720, and the electronics box 740 seen in FIG. 7 offer one configuration of parts of the intra-oral system 100. The intra-oral system 100 allows a user to manipulate a cursor 151 on a display.

Figure 8A:
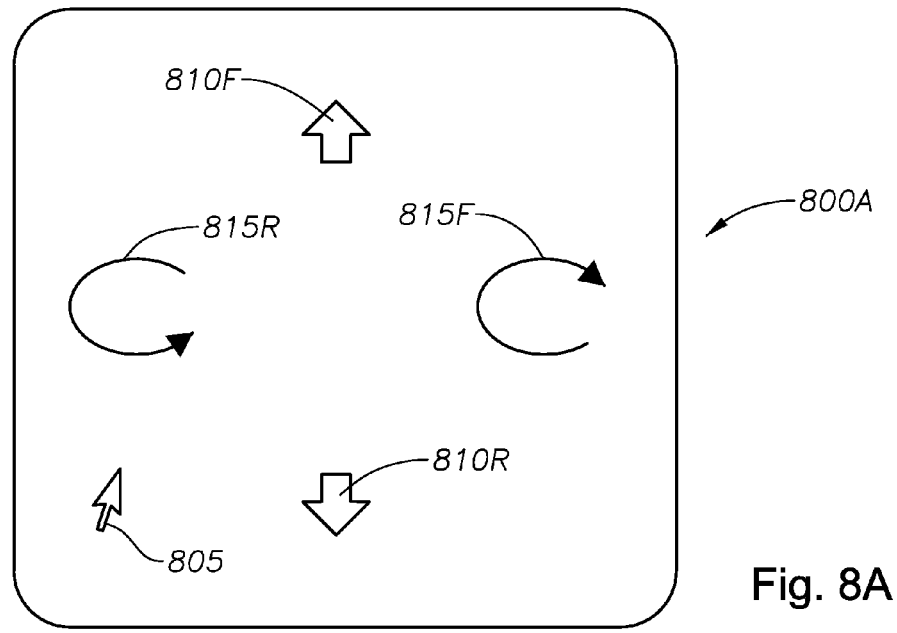
FIGS. 8A through 8C present various arrangements for displays from the system of FIG. 1.
Figure 8B:
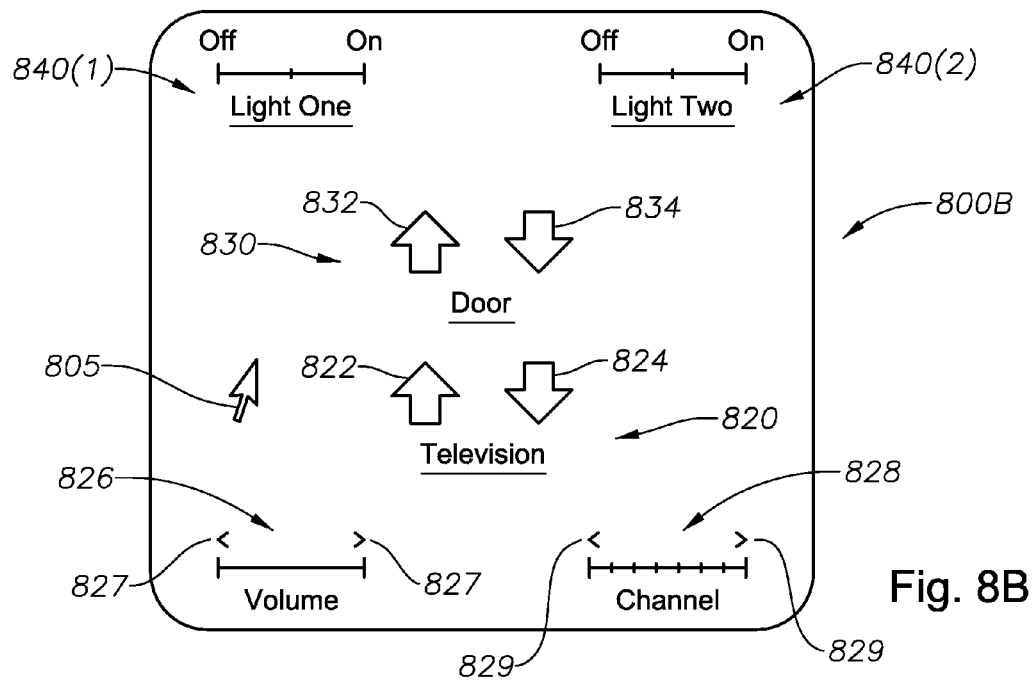
Figure 8C:
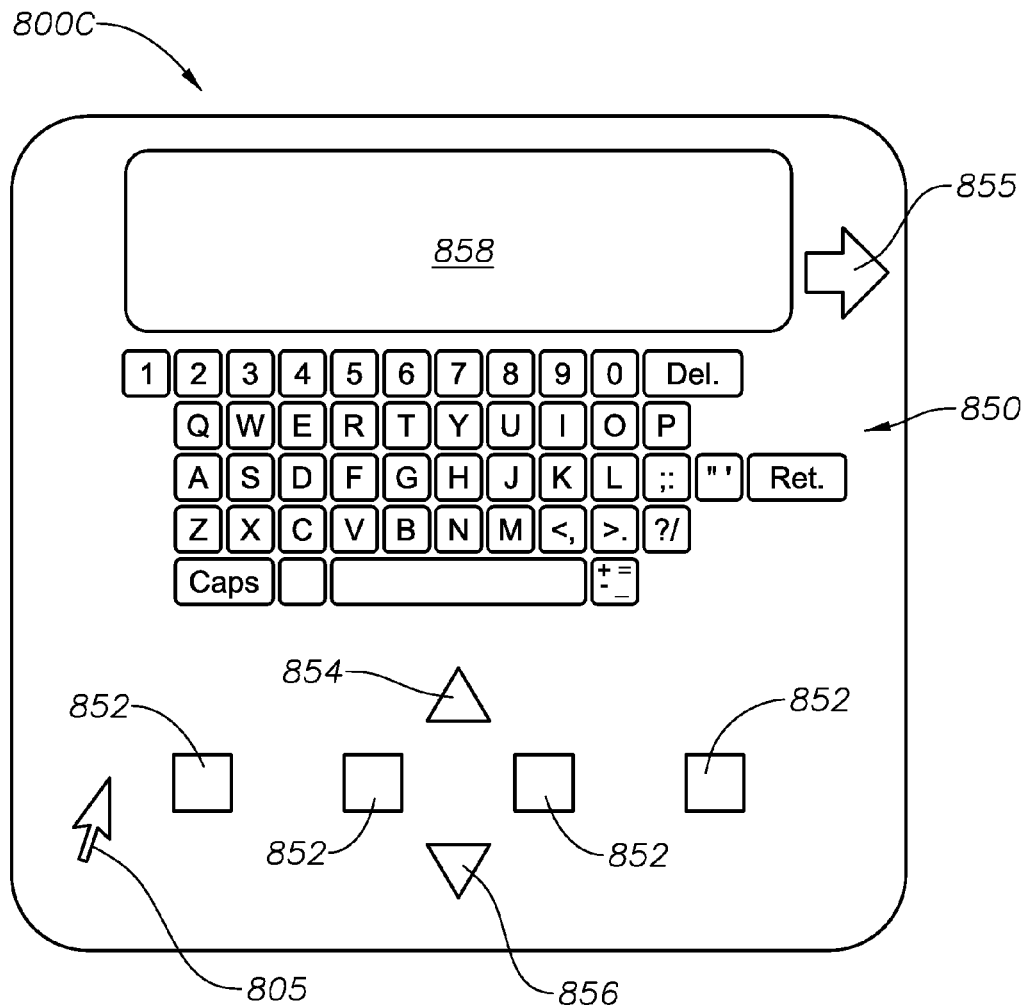

FIGS. 8A through 8C present various arrangements for displays from the system of FIG. 1. FIGS. 8A through 8C also demonstrate methods for using the head set 600 and attached mouthpiece (such as mouthpiece 110).

First, FIG. 8A demonstrates how the head set 600 and attached mouthpiece may be used for moving a mechanical object, in one embodiment. FIG. 8A specifically shows a display 800A. In this system, a cursor is shown at 805. The cursor 805 is used to move an object by the user through lingual manipulation in accordance with the pressure profile. As the user applies pressure to the various air cells in the bulb defining the mouthpiece, the cursor 805 is moved across the display 800A. Thus, the mouthpiece becomes a "mouth mouse."

The display 800A is arranged for the purpose of allowing the user to move an external object. In this instance, the individual may use the system 100 to operate a wheelchair. Alternatively, the individual may use the system 100 to manipulate the position of a bed or to open or close a door.

The display 800A may be opened by clicking on an application 158 from display 156 (shown in FIG. 1). Alternatively, the display 800A may be a dedicated display on a screen that does not change except when being powered up or down. The display 800A includes directional keys. In this arrangement, the directional keys are used to move a wheelchair (not shown). The illustrative directional keys represent forward 810F and reverse 810R arrows. Actuation of these arrows 810F, 810R causes the wheelchair (or other object) to move forward or backward. The directional keys also represent clockwise 815F and counter-clockwise 815R arrows. Actuation of these arrows 815F, 815R causes the wheelchair to rotate clockwise or counter-clockwise, respectively.

The keys 810F, 810R, 815F, 815R are activated by using the cursor 805. In one aspect, a symbol 810F, 810R, 815F, or 815R is activated by the user positioning the cursor 805 over the selected symbol 810F, 810R, 815F, 815R, and then double-clicking on the center cell 115 or a center of the mouthpiece 310 or 410. In another aspect, a symbol 810F, 810R, 815F, or 815R is activated by the user positioning the cursor 805 over the selected symbol 810F, 810R, 815F, 815R, and then pressing against the center cell 115 for a designated period of time at a certain level of pressure. In the instance where the center cell 115 is "dead" or where there is no center cell, a symbol 810F, 810R, 815F, or 815R may be activated by the user positioning the cursor 805 over the selected symbol 810F, 810R, 815F, 815R, and then pressing the center of the mouthpiece 110, 310, or 410 for a designated period of time at a certain level of pressure.

It is understood that the idea of "clicking" as presented herein is not the traditional action taken by a user who is operating a computer. The individual who has functional use of his or her hands is able to double-press a touch pad or double-click a so-called mouse in order to access a link or make an on-screen selection. In the present application, the user is using his or her tongue. The methods herein are not limited as to how "clicking" is recognized by the first processor. Preferably, the first processor recognizes a selection or "clicking" when the user applies a pre-selected number of pressure applications, i.e., two, against a designated portion of the mouthpiece in quick succession, or double-clicks and holds the pressure to maintain actuation.

The display 800A of FIG. 8A is ideally supported on the individual's wheelchair. For example, the display 800A will be mounted on an arm rest (not shown). At the same time, the mouthpiece 110 is part of the head set 600 so that the mouthpiece 110 is at all times in proximity to the user's mouth. In this way, the individual may selectively insert the mouthpiece 110 into their mouth for movement of the wheelchair (or other object).

It is understood in this application that the second processor 150 will be in electrical communication with a motor or servo-system on the wheelchair. In this way, the user's instructions delivered by moving the cursor 805 on the screen 800A cause the wheelchair to respond. Of course, the display 800A may be used to control appliances other than a wheelchair. For example, symbols 810F, 810R, 815F, 815R may be used to adjust a mechanically-controlled bed, open and close a door, and the like.

The system 100 may alternatively be used by a physically-limited individual to operate other apparatus' besides a mechanical appliance. Such apparatus' may include electrical appliances such as a television, a light fixture, a radio, or a thermostat.

FIG. 8B presents a display 800B for the system 100, in an alternate embodiment. A cursor is again shown at 805. The cursor 805 is used to change the status of an electrical appliance by the user through lingual manipulation in accordance with the pressure profile. The display 800B shows arrow 822 for turning on a television, and arrow 824 for turning off a television. The display 800B also shows carrots 827 for adjusting the volume of the television, and carrots 729 for changing the channel.

The display 800B also shows bar 840(1) for turning a first light fixture on and off, and bar 840(2) for turning a second light fixture on and off. The bar configuration 840(1) and 840(2) may also serve as a rheostat, thereby adjusting the brightness of a light fixture. The display 800B also shows arrow 832 for opening a door, and arrow 834 for closing the door. This would be done through a servo-motor.

It is understood that displays 800A and 800B are merely illustrative. Other appliances may be controlled through the use of a cursor and symbols. The user may then press or double-click on the center air cell 115 of the mouthpiece 110 or in the center of a mouthpiece such as mouthpieces 310, 410 to turn an object on or off or to adjust its status. A wireless signal is then sent from the transceiver 155 to the appliance using infrared technology, Bluetooth technology or other wireless technology that may be known to those of ordinary skill in the art.

FIG. 8C presents a display 800C for the intra-oral system 100, in yet an alternate embodiment. In this display 800C, a cursor is again shown at 805. The illustrative cursor 805 is an arrow. The cursor 805 is moved across the display 800C in accordance with the pressure profile. In this embodiment, the display 800C includes a keyboard 850. The keyboard 850 and other symbols in the display 800C are used to allow the individual to type text messages, update contacts, operate a web browser, or interface with a website using just his or her mouth.

The display 800C includes symbols 852. These symbols 852 may be used, for example, to open and close a door (not shown) or to select an appliance to be controlled. Arrow keys 854, 856 are also provided on the display 800C. The user may manipulate a selected electrical appliance by double-clicking on an arrow key 854, 856. For example, a light fixture may be brightened or dimmed by double-clicking on the arrow keys 854, 856. Alternatively, the channel of a television or radio may be changed by double-clicking on the arrow keys 854, 856. Separate arrow keys (not shown) may be used to then adjust the volume.

In lieu of double-clicking, a symbol 852 or an arrow key 854, 856, a function may be selected or activated by the user positioning the cursor 805 over the selected symbol 852 or arrow 854, 856, and then pressing against the center cell 115 for a designated period of time at a certain level of pressure. In the instance where the center cell 115 is "dead" or there is no center cell, a selected symbol 852 or key 854, 856 may be activated by the user positioning the cursor 805 over the selected symbol 852 or arrow key 854, 856, and then pressing against a designated radial cell 118, 318, 418 or in the centerpoint of the mouthpiece 110, 310, 410 for a designated period of time at a certain level of pressure.

A signal is sent from the system 100 to the electrical apparatus. For example, a wireless signal may be sent from transceiver 155 to the appliance. This signal is preferably a wireless signal such as through infrared technology, Bluetooth technology or other wireless technology that may be known to those of ordinary skill in the art.

The keyboard 850 allows the physically-limited individual to type in a text message or to send an e-mail message to another individual. In addition, the keyboard 850 allows the physically-limited individual to update contacts or to navigate web sites. The individual uses the cursor 805 to select alpha-numeric keys to be "pressed." Pressing means double-clicking or otherwise applying pressure to a selected air or fluid cell in the mouthpiece 110, 310, 410. By selecting and "pressing" a series of digital keys on the keyboard 850, text may be "typed."

It is preferred that a visualization screen 858 be provided on the display 800C. The visualization screen 858 allows the user to see what text is being typed. Once a message is composed or a query is presented, the message or query may be "sent" by pressing a return arrow 855. In this arrangement, the second processor 150 has a wired or wireless internet connection for delivering the message through a communications network.

Figure 9A:
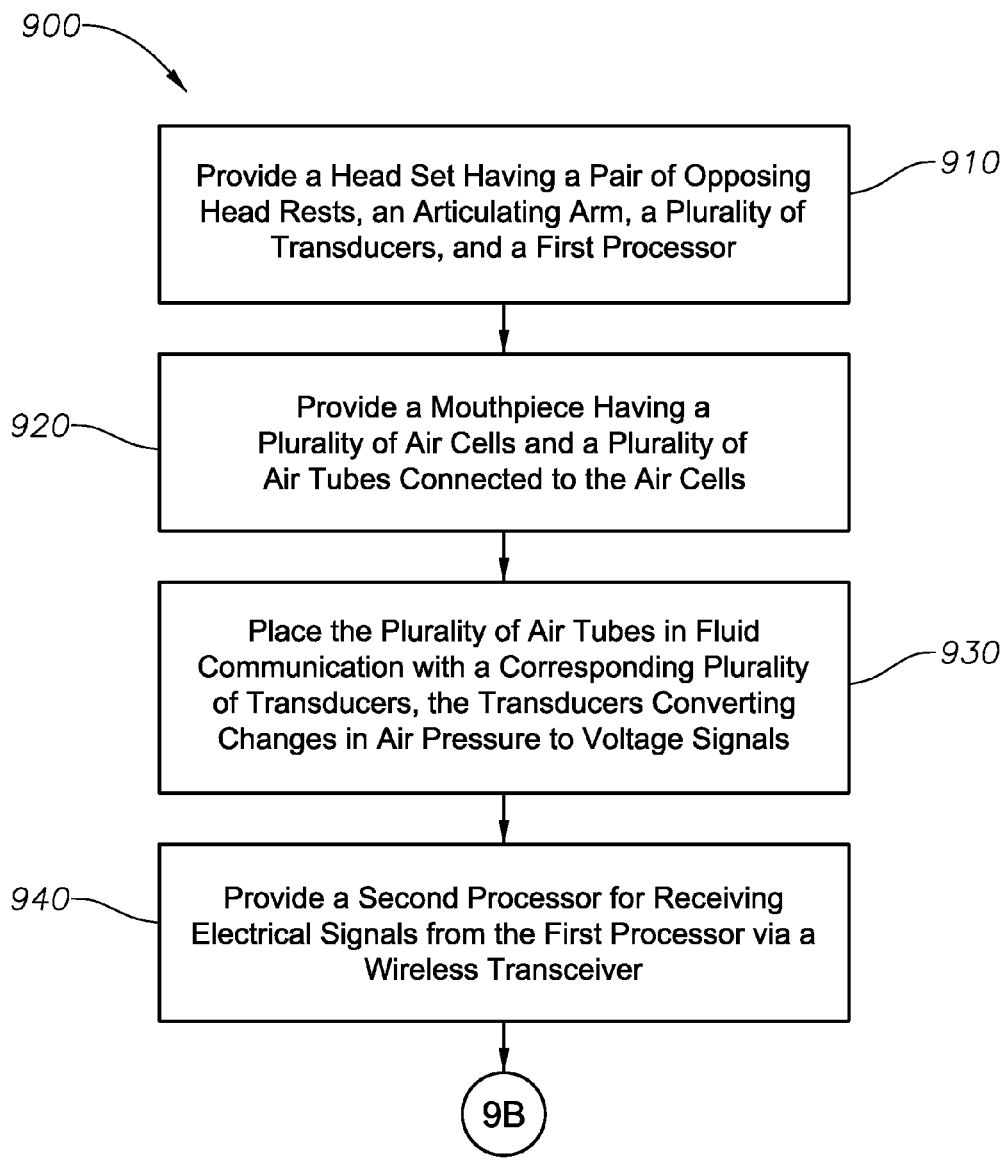
FIGS. 9A and 9B provide a single flowchart for a method for moving a cursor on a display using lingual manipulation, in one embodiment. The flowchart offers alternate final steps for causing an external action.
Figure 9B:
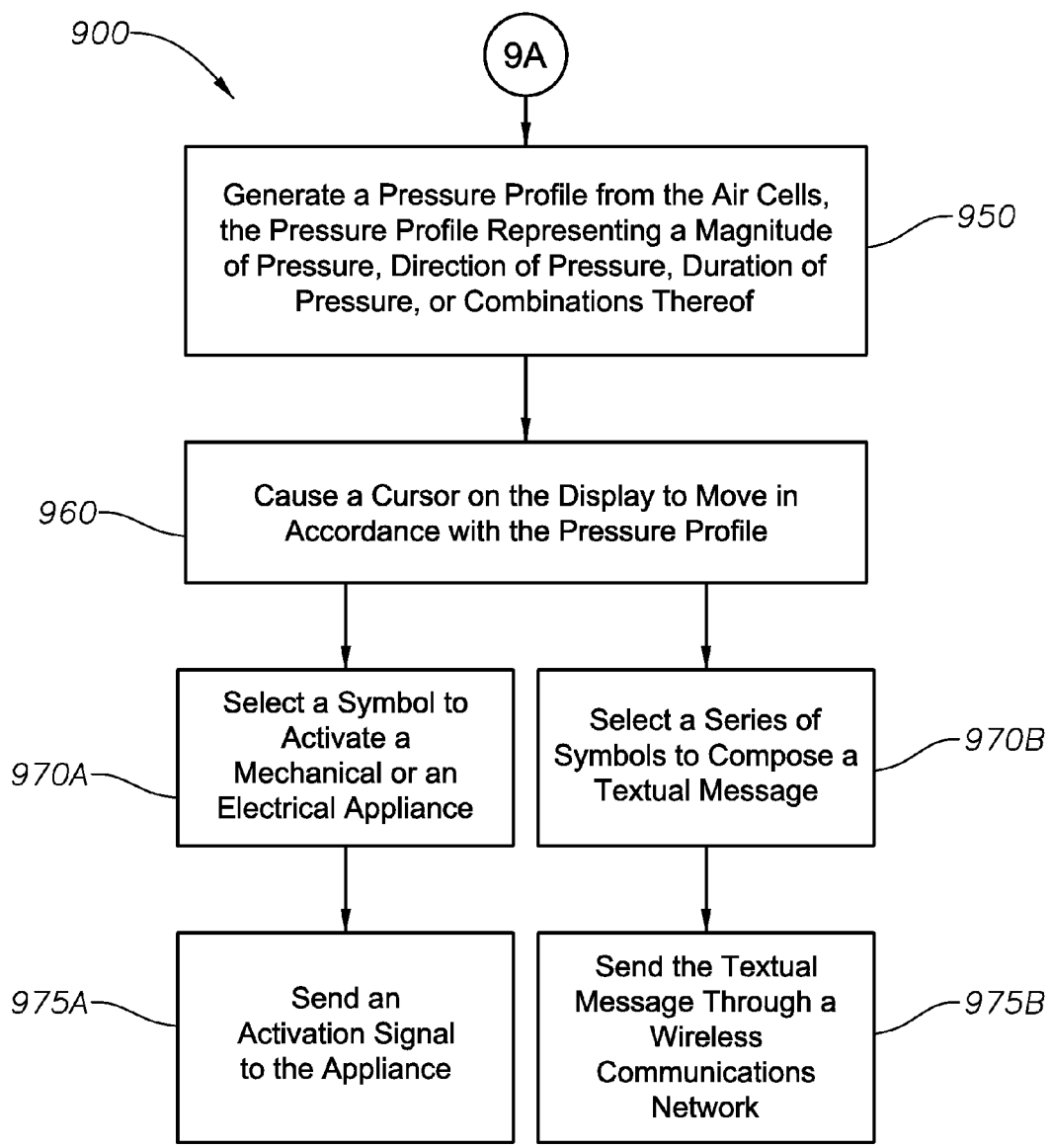

A method 900 for moving a cursor on a display using lingual manipulation is also provided herein. FIGS. 9A and 9B present a flow chart, showing steps for generally performing the method 900, in one embodiment.

The method 900 first includes providing a head set. This is shown at Box 910 of FIG. 9A. The head set is generally in accordance with the head set 600 described above, in its various embodiments. Generally, the head set will have a head piece and opposing head rests. The head set will also have an articulating arm extending from the head piece.

The method 900 further includes providing a mouthpiece. This is seen at Box 920. The mouthpiece is part of the head set, and serves as a "mouth mouse." The mouthpiece defines an elastomeric bulb and is connected proximate a distal end of the articulating arm.

In one aspect, the mouthpiece comprises at least three outer cells disposed radially around a centerpoint. The centerpoint may define a separate cell, or it may be a "dead" area. Alternatively, the mouthpiece has four, five, or more cells disposed radially around the bulb in either an eccentric or a concentric design. The cells are divided and sealed by walls.

The mouthpiece has a plurality of fluid-containing cells. The fluid may be a compressible fluid, or gas. The compressible fluid may be air or another non-toxic gas. Alternatively, the fluid may be a substantially non-compressible fluid, such as water or other non-toxic liquid. A combination of compressible and non-compressible fluids may also be employed. In any aspect, the fluid-containing cells are embedded into the mouthpiece for receiving pressure applied by the tongue of an individual.

The head set will also include a plurality of tubes. Each tube has a proximal end and a distal end, with the distal end of each of the tubes being in substantially sealed fluid communication with a corresponding cell of the mouthpiece. In one aspect, each of the tubes comprises more than one tubular body operatively connected to form a single, pneumatically or fluidically sealed channel. In this instance, a manifold may be used to provide a "quick-connect" between sets of tubes.

Preferably, each of the plurality of tubes is an air tube that resides substantially at ambient pressure. Alternatively, each of the plurality of tubes may be preloaded at a pressure of about 15 psi to 25 psi. This creates desirable additional resistance for stronger users. It also provides flexibility for the operator in "tuning" the system so that pressure readings are accurate. The tubes preferably have an inner diameter of about 0.05 inches to 0.5 inches. However, other dimensions may be employed.

The head set also includes a plurality of transducers. Each transducer is preferably a pressure sensor having a diaphragm that is sensitive to changes in pressure within a corresponding tube. The transducers convert changes in pressure within the cells to voltage or other electrical signals. The head set further includes a first processor. The first processor receives the voltage (or other raw electrical) signals from the transducers and processes them.

The method 900 also comprises placing each of the plurality of tubes in fluid communication with a corresponding transducer. This is provided at Box 930. More specifically, each transducer is in sealed fluid communication with the proximal end of a corresponding tube. The changes in pressure within the cells are delivered pneumatically or fluidically to the transducers through the respective tubes.

Of interest in the method 900, the transducers are mechanically supported by the head rest. Preferably, each transducer resides within an electronics box, such as box 730 of FIG. 7. In this instance, the electronics box will include a manifold that allows air tubes to be connected to nozzles external to the electronics box for providing the needed fluid communication with the transducers.

The method 900 also includes the step of providing a second processor. This is shown in Box 940. The second processor is in electrical communication with the first processor via a wireless transceiver. The second processor may be a micro-computer such as a personal digital assistant or a tablet. Alternatively, the second processor may be a part of a laptop computer or a desktop computer.

The second processor is in operative electrical communication with a display. The display has a visual output that presents a cursor.

The method 900 also includes the step of generating a pressure profile from the cells. This step is provided in Box 950 of FIG. 9B. The pressure profile is generated by the first processor in response to the voltage or other electrical signals received from the transducers. The signals are modulated by the first processor to generate a pressure profile from the cells. Preferably, the pressure profile represents a magnitude of pressure within the cells, a direction of pressure, a duration of pressure, or combinations thereof.

The pressure profile is based upon pressure readings from the various cells. In one aspect, pressure signals are processed such that each voltage signal represents an air pressure reading from a corresponding air cell. Voltage signals from one or more corresponding transducers are averaged over a specified period of time to produce the pressure profile. The pressure profile has a peak indicative of location at which pressure is being generated within the one or more cells during the specified period of time.

The first processor sends signals based on pressure profiles to the second processor. The signals are wireless signals that are sent to the transceiver of the second processor. Visualization software is pre-loaded onto the second processor unit to enable the user to see a cursor being moved on the display. The second processor interprets the command signals from the first processor, and is able to move a cursor on a display.

The method 900 further includes the step of causing the cursor on the display of the second processor to move. This is provided at Box 960. The cursor is moved by means of lingual manipulation of the mouthpiece. More specifically, the user applies pressure to the various cells in the mouthpiece to ultimately cause translation of the cursor on the display.

In one aspect, the cursor is moved over a symbol that represents a mechanical device to be activated or an electrical appliance to be changed. The symbol on the display may be of any type. For example, the symbol may be a picture of an apparatus or appliance. Alternatively, the symbol may be one or more alphanumeric characters, an arrow indicating direction, or a geometric figure.

In order to move a cursor, a magnitude of each voltage signal is recorded as part of the pressure profile over the specified period of time. The object is then caused to be moved on the display in the direction indicated by the pressure profile, optionally at a velocity that corresponds to the magnitude of the voltage signals. In another aspect, an application of pressure by a user on the centerpoint for a specified period of time and at a specified magnitude causes a location of the object to be reset to a beginning point on the display. Alternatively, an application of pressure by a user on a designated outer cell for a specified period of time and at a specified magnitude causes a location of the object to be moved to a corresponding location on the display.

Optionally, the method 900 includes selecting a symbol to actuate a mechanical device or an electrical appliance. This is shown at Box 970A. Alternatively, a series of symbols is selected in order to compose a textual message. This is shown at Box 970B.

To select a symbol, the cells within the mouthpiece may be configured to respond to double-clicking by the user. This means that the user moves his or her tongue against a particular cell or area of the mouthpiece twice within a designated period of time recognized by the processor. For example, double-clicking of application of pressure by a user on a centerpoint for a specified period of time and at a specified magnitude may cause actuation of a mechanical device or an electrical appliance, as discussed above. Alternatively, the user may simply hold pressure against the centerpoint for a specified longer period of time and at a specified magnitude over a symbol on the display. An activation signal is then sent to the appliance. This is provided at Box 975A.

As an additional step to Box 970B, the user may send the textual message through a wireless communications network. This is shown at Box 975B. This sending step may be done by the user "clicking" on a return key or other symbol. The textual message may be a text message, an e-mail, or a web-based query.

As can be seen, a unique head set is offered that allows an individual to move a cursor or to change the state of an appliance through lingual manipulation of a mouthpiece. The inventions allow a user who has limited or no functional use of his or her upper extremities to use a "mouth mouse." It is understood that the configurations of the mouthpiece, the head set, and the articulating arm provided herein are merely illustrative. Other designs and arrangements for a head set may be employed. For example, the head set may be in the form of a hat, meaning that it includes a covering for the crown of the user's head. This may be beneficial in providing support for the manifold, for the electrical circuit board, and for the tubes as they wrap around behind the head set. However, what is important is that the head set be designed to allow the mouthpiece to reach the mouth of the user.

In addition, other designs for a mouthpiece may be employed. For example, the mouthpiece may only have, for instance, two cells placed in side-by-side relation. In another arrangement, the mouthpiece does not use cells, tubes and pressure sensors, but instead operates on a system where electrical signals are sent directly from the mouthpiece. The mouthpiece may be arranged in a matrix, with pressure sensors being embedded directly into the mouthpiece within cells defined by the matrix. The pressure sensors may be tactile pressure sensors that detect pressure applied by the patient's tongue as the patient moves his or her tongue across the bottom surface of the bulb. The sensor may measure duration of pressure, direction of pressure, magnitude of pressure, or combinations thereof, at various cell locations.

Additional sensing means may be incorporated into each cell in order to sense direction of pressure. In addition, a clock may be associated with each signature signal to measure duration of a detected signal.

While it will be apparent that the inventions herein described are well calculated to achieve the benefits and advantages set forth above, it will be appreciated that the inventions are susceptible to modification, variation and change without departing from the spirit thereof.

I claim:

1. A head set for facilitating movement of an object through lingual manipulation, the head set comprising:
 a head piece;
 an arm extending from the head piece and having a distal end;
 an elastomeric mouthpiece comprising a bulb, the bulb being connected proximate the distal end of the arm, and the bulb having a plurality of fluid-containing cells embedded therein configured to respond to pressure applied by the tongue of an individual when the mouthpiece is in a mouth of the individual;
a plurality of tubes, each tube having a proximal end and a distal end, with the distal end of each of the tubes being in substantially sealed fluid communication with a corresponding cell, and the proximal end being in substantially sealed fluid communication with a respective transducer, wherein:
each transducer is configured to convert changes in pressure within the cells to electrical signals, and
each transducer is mechanically supported by the head set;
a first processor for processing the electrical signals, wherein the electrical signals are modulated to generate a pressure profile from the cells; and
a transmitter for sending wireless signals from the first processor to a second processor in accordance with the pressure profile, wherein:
the second processor is in electrical communication with a cursor on a display, and
the second processor is programmed to cause the cursor to move across the display in response to the wireless signals received from the transmitter.

2. The head set of claim 1, wherein:
each cell and each tube contains (i) a compressible fluid, (ii) a non-toxic incompressible fluid, or (iii) a combination thereof.

3. The head set of claim 2, wherein:
each cell and each tube contains a compressible fluid; and
the compressible fluid comprises air, oxygen, carbon dioxide, nitrogen, or combinations thereof.

4. The head set of claim 2, wherein:
each cell and each tube contains a non-toxic incompressible fluid; and
the incompressible fluid comprises water.

5. The head set of claim 2, wherein the mouthpiece is fabricated from polyisoprene rubber, silicone, chloroprene rubber, neoprene, styrene butadiene rubber, acrylonitrile butadiene rubber, ethylene propylene diene methylene, polyvinylchloride, polyethylene, polyurethane, urethane-coated nylon, ethyl vinyl acetate, and combinations thereof.

6. The head set of claim 2, wherein the bulb comprises at least three outer cells disposed radially around a centerpoint.

7. The head set of claim 6, wherein the centerpoint defines a separate central cell in fluid communication with one of the plurality of tubes.

8. The head set of claim 2, wherein each of the plurality of tubes has an inner diameter of about 0.05 inches to 0.5 inches.

9. The head set of claim 2, wherein each of the plurality of tubes resides substantially at ambient pressure.

10. The head set of claim 2, wherein the pressure profile represents a magnitude of pressure within cells, a direction of pressure, a duration of pressure, or combinations thereof.

11. The head set of claim 2, wherein each of the plurality of transducers is a pressure sensor having a diaphragm that is sensitive to changes in pressure within a tube.

12. The head set of claim 2, wherein the first processor receives electrical signals from each of the plurality of transducers and processes those signals such that each electrical signal represents a pressure reading from a corresponding cell or from the combined cells.

13. The head set of claim 12, wherein the first processor receives each of the electrical signals, and averages the signals over a specified period of time to produce the pressure profile, the pressure profile having a peak indicative of location at which pressure is being generated within the one or more cells during the specified period of time.

14. The head set of claim 12, wherein the electrical signals are voltage signals.

15. The head set of claim 12, wherein each of the transducers comprises an analog-to-digital converter, such that the electrical signals are digital signal values.

16. The head set of claim 2, wherein the head piece comprises a pair of opposing head rests, with at least one of the head rests being adjustable relative to the head piece.

17. The head set of claim 2, wherein the arm is an articulating arm that comprises:
a first arm portion extending from one of the opposing head rests, and comprising a pivot point away from the head rest; and
a second arm portion connected to the pivot point, and having the distal end away from the pivot point.

18. The head set of claim 2, wherein the head piece is configured such that the first arm portion may be selectively connected to either of the opposing head rests.

19. The head set of claim 2, wherein each of the plurality of tubes comprises more than one tubular body operatively connected through a manifold to form individual, fluidically sealed channels.

20. The head set of claim 2, wherein the second processor is a personal digital assistant, a tablet, a laptop computer, or a desktop computer.

21. The head set of claim 2, wherein the second processor comprises a transceiver for receiving wireless signals from the transmitter; and is in electrical communication with (i) a motor for moving an object, (ii) a switch for changing a state of an electrical appliance, or (iii) both.

22. The head set of claim 2, wherein:
the second processor comprises a transceiver for receiving wireless signals from the transmitter, and is in electrical communication with a motor for moving a mechanically-controlled appliance; and
the appliance is a bed, a wheelchair, or a door.

23. The head set of claim 2, wherein:
the second processor comprises a transceiver for receiving wireless signals from the transmitter, and is in electrical communication with a switch for changing the state of an electrical appliance; and
the switch controls a light fixture, a television, or a thermostat.

24. The head set of claim 2, wherein the bulb comprises at least three outer cells disposed radially and concentrically around a centerpoint.

25. The head set of claim 2, wherein the bulb comprises at least three outer cells disposed radially and eccentrically around a centerpoint.

26. A method for moving a cursor on a display using lingual manipulation, comprising:
providing a head set for a user, the head set comprising:
a head piece;
an arm extending from the head piece and having a distal end;
an elastomeric mouthpiece comprising a bulb, the bulb being connected proximate the distal end of the arm, and the bulb having a plurality of fluid-containing cells embedded therein for receiving pressure applied by the tongue of a user;
a plurality of tubes, each tube having a proximal end and a distal end, with the distal end of each of the tubes being in substantially sealed fluid communication with a corresponding cell, and the proximal end being in substantially sealed fluid communication with a respective transducer wherein:

each transducer converts changes in pressure within the cells to electrical signals, and each transducer is mechanically supported by the head set;

a first processor for processing the electrical signals, wherein the electrical signals are modulated to generate a pressure profile from the cells;

a transmitter;

placing the plurality of tubes in fluid communication with the corresponding plurality of transducers; and placing the first processor in operative electrical communication with the second processor, wherein the second processor:

is in electrical communication with a cursor on a display, and is programmed to cause the cursor to move across the display in response to wireless electrical signals received form the transmitter in accordance with the pressure profile.

27. The method of claim 26, wherein:

each cell and each tube contains (i) a compressible fluid, (ii) a non-toxic incompressible fluid, or (iii) a combination thereof.

28. The method of claim 27, wherein the compressible fluid comprises air, oxygen, carbon dioxide, nitrogen, or combinations thereof.

29. The method of claim 27, wherein the incompressible fluid comprises water.

30. The method of claim 26, wherein the mouthpiece is fabricated from polyisoprene rubber, silicone, chloroprene rubber, neoprene, styrene butadiene rubber, acrylonitrile butadiene rubber, ethylene propylene diene methylene, polyvinylchloride, polyethylene, polyurethane, urethane-coated nylon, ethyl vinyl acetate, and combinations thereof.

31. The method of claim 26, wherein the bulb comprises at least three outer cells disposed radially around a centerpoint.

32. The method of claim 26, wherein the pressure profile represents a magnitude of pressure within the cells, a direction of pressure, a duration of pressure, or combinations thereof.

33. The method of claim 26, wherein each of the plurality of tubes has an inner diameter of about 0.05 inches to 0.5 inches.

34. The method of claim 26, wherein each of the plurality of transducers is a pressure sensor having a diaphragm that is sensitive to changes in pressure within a tube.

35. The method of claim 26, wherein the first processor receives electrical signals from each of the plurality of transducers and processes those signals such that each electrical signal represents a pressure reading from a corresponding cell or from the combined cells.

36. The method of claim 35, wherein the first processor receives each of the electrical signals, and averages the signals over a specified period of time to produce the pressure profile, the pressure profile having a peak indicative of location at which pressure is being generated within the one or more cells during the specified period of time.

37. The method of claim 35, wherein each of the transducers comprises an analog-to-digital converter, such that the electrical signals are digital signal values.

38. The method of claim 27, wherein the head piece comprises a pair of opposing head rests, with at least one of the head rests being adjustable relative to the head piece.

39. The method of claim 26, wherein:

the head set further comprises a manifold;

each of the plurality of tubes comprises a jumper portion between a respective transducer and the manifold, and a mouthpiece portion between the manifold and the mouthpiece; and placing the plurality of tubes in fluid communication with the corresponding plurality of transducers comprises connecting the mouthpiece portion of each of the tubes to the manifold.

40. The method of claim 26, wherein:

the second processor is a personal digital assistant, a tablet, a laptop computer, or a desktop computer;

the transmitter is a first transceiver; and the first transceiver communicates wirelessly with a second transceiver associated with the second processor.

41. The method of claim 26, further comprising:

selecting a symbol on the display to actuate a mechanical or an electrical appliance.

42. The method of claim 41, wherein the second processor is configured such that the user may click on a symbol on the display by applying pressure on a centerpoint of the mouthpiece for a specified period of time and at a specified magnitude.

43. The method of claim 41, wherein the symbol on the display comprises a picture, one or more alphanumeric characters, an arrow, or a geometric figure.

44. The method of claim 41, wherein:

the processor is in electrical communication with a motor for moving a mechanical appliance; and the symbol on the display corresponds to the appliance.

45. The method of claim 44, wherein the appliance is a bed, a wheelchair, or a door.

46. The method of claim 41, wherein:

the processor is in electrical communication with a switch for changing an electrical state of an appliance; and the symbol on the display corresponds to the appliance.

47. The method of claim 46, wherein the appliance is a light fixture, a television, or a thermostat.

48. The method of claim 26, wherein the display comprises:

a virtual keyboard such that a user may select a series of characters on the keyboard using their tongue to compose a textual message; and a "send" symbol that, when selected by the user, the textual message is sent through a wireless communications system.

49. A method of typing characters on a virtual keyboard using lingual musculature, comprising:

wearing a head set on a head, the head set comprising:

a head piece;

an articulating arm extending from the head piece and having a distal end;

an elastomeric mouthpiece comprising a bulb, the bulb being connected proximate the distal end of the articulating arm, and the bulb having a plurality of fluid-containing cells embedded therein and configured for receiving pressure applied by the tongue of a user when the mouthpiece is in a mouth of the user;

a plurality of tubes, each tube having a proximal end and a distal end, with the proximal end of each of the tubes being in substantially sealed fluid communication with a corresponding plurality of transducers for converting changes in pressure within the cells to electrical signals, and with the distal end of each of the tubes being in substantially sealed fluid communication with a corresponding cell, wherein:

each transducer converts changes in pressure within the cells to electrical signals, and each transducer is mechanically supported by the head set;
a first processor for processing the electrical signals, wherein the electrical signals are modulated to generate a pressure profile from the cells, the pressure profile representing a magnitude of pressure within the cells, a direction of pressure, a duration of pressure, or combinations thereof;
a transmitter;

placing the mouthpiece in one's mouth;

moving one's tongue across a bottom surface of the mouthpiece so as to apply pressure to cells of the mouthpiece in order to move a cursor on a display, the display having a digital keyboard associated with a second processor that receives the electrical signals via a wireless communications system, and the cursor moving across the digital keyboard in accordance with the pressure profile;

using the cursor to select characters on the digital keyboard; and clicking on selected characters on the digital keyboard using lingual musculature on the mouthpiece in order to compose a textual message.

50. The method of claim 49, wherein:

applying pressure to the cells causes changes in air pressure within the plurality of tubes, such changes being sensed by each of the plurality of transducers and converted to an electrical signal.

51. The method of claim 50, wherein each of the plurality of transducers is a pressure sensor having a diaphragm that is sensitive to changes in pressure within a tube.

52. The method of claim 51, wherein the signal processor receives electrical signals from each of the plurality of transducers and processes those signals such that:

each electrical signal represents a pressure reading from a corresponding cell; and electrical signals from one or more corresponding cells are averaged over a specified period of time to produce the pressure profile, the pressure profile having a peak indicative of location at which pressure is being generated within the one or more cells during the specified period of time.

53. The method of claim 51, wherein:

each cell and each tube contains (i) a compressible fluid, (ii) a non-toxic incompressible fluid, or (iii) a combination thereof.

54. The method of claim 50, wherein:

the second processor is a personal digital assistant, a tablet, a laptop computer, or a desktop computer;

the transmitter is a first transceiver; and the first transceiver communicates wirelessly with a second transceiver associated with the second processor.

* * * * *